United States Patent [19]

Kokusho et al.

[11] Patent Number: 4,783,402
[45] Date of Patent: Nov. 8, 1988

[54] PRODUCTION OF PRIMARY OR SECONDARY ALCOHOL DERIVATIVES OF PHOSPHOLIPIDS BY THE ENZYMATIC TECHNIQUE

[75] Inventors: Yoshitaka Kokusho, Kunitachi; Shigeaki Kato; Haruo Machida, both of Hino, all of Japan

[73] Assignee: Meito Sangyo Kabushiki Kaisha, Aichi, Japan

[21] Appl. No.: 598,697

[22] Filed: Apr. 10, 1984

[30] Foreign Application Priority Data

Apr. 11, 1983 [JP] Japan .................................. 58-63304
Apr. 11, 1983 [JP] Japan .................................. 58-63305

[51] Int. Cl.[4] ...................... C12P 33/00; C12P 19/40; C12P 19/30; C12P 9/00
[52] U.S. Cl. ...................................... 435/52; 435/68; 435/89; 435/92; 435/106; 435/113; 435/115; 435/120; 435/121; 435/122; 435/125; 435/127; 435/128; 435/118; 435/131
[58] Field of Search ............... 435/155, 128, 195, 196, 435/52, 117, 131, 87, 88, 89, 72, 74, 118, 92, 120, 68, 121, 131, 122, 125

[56] References Cited

FOREIGN PATENT DOCUMENTS 1581810 4/1978 United Kingdom .

OTHER PUBLICATIONS

Fauvel, J. et al, Studies on Glycerophospholipids, Biochim. Biophys. Acta, vol. 792 pp. 72–78, Jan. 17, 1984.
M. Kates, "Lecithinase Systems in Sugar Beet, Spinach, Cabbage, and Carrot, Can. J. Biochem. Physiol., 32 (1954) 571–583.
R. M. C. Dawson, "The Formation of Phosphatidylglycerol and Other Phospholipids by the Transferase Activity of Phospholipase D," Biochem., J., 102, (1967) 205–210.
S. Kovatchev, "The Preparation of Phospholipids by Phospholipase D," Adv. Exp. Med. Biol., 101 (1978), 221–226.
M. M. Rokhimov, "Enzymic Synthesis of Phospholipids at a Phase Interface," Chem. Abstract, vol. 91, (1979) p. 278.

*Primary Examiner*—Blondel Hazel
*Attorney, Agent, or Firm*—Sherman & Shalloway

[57] ABSTRACT

A process for producing a primary or secondary alcohol derivative of a phosopholipid which comprises reacting the phospholipid with a primary or secondary alcohol in the presence of phospholipase DM.

5 Claims, No Drawings

PRODUCTION OF PRIMARY OR SECONDARY ALCOHOL DERIVATIVES OF PHOSPHOLIPIDS BY THE ENZYMATIC TECHNIQUE

This invention relates to primary or secondary alcohol derivatives of phospholipids and a process for production thereof by an enzymatic technique.

The process of this invention can produce a broad range of primary or secondary alcohol derivatives of phospholipids including those primary or secondary alcohol derivatives of phospholipids which have heretofore been considered impossible of production by an enzymatic technique. It has only been known that secondary alcohol derivatives of phospholipids in particular cannot be formed by the enzymatic technique.

Particularly this invention relates to a process for producing a primary or secondary alcohol derivative of a phospholipid, which comprises reacting a phospholipid with a primary or secondary alcohol in the presence of phospholipase DM having an optimum temperature of 60° to 70° C. and an optimum pH of about 7 which differs from the known cabbage-derived phospholipase D (optimum temperature not more than 40° C., optimum pH 5.4–5.6) used heretofore in the enzymatic technique; and to the primary or secondary alcohol derivative of the phospholipid obtained by the above process.

In the present application, the term "primary or secondary alcohol derivative of a phospholipid" denotes a new phospholipid different from the starting phospholipid, which is formed by hydrolyzing the ester linkage between the phosphoric acid structural moiety of the starting phospholipid and its alcohol structural moiety under the action of phospholipase DM, and simultaneously transferring the phosphatidic acid structural moiety to the primary or secondary alcohol used in the reaction.

More specifically, this invention pertains to a process for producing a primary or secondary alcohol derivative of a phospholipid represented by the following formula (I)

$$A-O-\overset{O}{\underset{OH}{\overset{\|}{P}}}-O-R \qquad (I)$$

wherein A and R are as defined below, which comprises reacting a phospholipid represented by the following formula (II)

$$A-O-\overset{O}{\underset{OH}{\overset{\|}{P}}}-O-B \qquad (II)$$

wherein A is a moiety represented by the following formula (i)

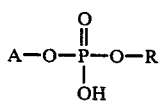   (i)

or the following formula (ii)

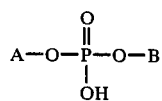   (ii)

in which $R_1$ and $R_2$ both represent $-O-COR_{11}$ or $-O-R_{12}$, or $R_1$ and $R_2$ in formula (i) together represent

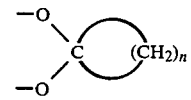

in which n represents a number of from 11 to 19, and $R_{11}$ and $R_{12}$ are identical or different and each represents a saturated or unsaturated aliphatic hydrocarbon group having 7 to 21 carbon atoms, and
B represents the group $-(CH_2)_2N^+(CH_3)_3$, $-(CH_2)_2NH_2$, $-CH_2CH(NH_2)COOH$, $-CH_2CH_2NH(CH_3)$, $-CH_2CH_2N(CH_3)_2$, $-CH_2CHOHCH_2OH$ or $-(CH_2)_mH$ in which m represents a number of from 1 to 5,
with a primary or secondary alcohol selected from the group consisting of (1) primary alcohols containing a residue R of a saturated or unsaturated aliphatic or aromatic hydrocarbon having 6 to 26 carbon atoms (excepting hexanol), said hydrocarbon residue being optionally substituted by a substituent selected from the class consisting of halogen, amino, acetyl, carboxyl and hydroxyl, or a residue R of said aliphatic or aromatic hydrocarbon having in the molecule a linkage selected from ether, ester and amide linkages, (2) primary alcohols having a residue R of a pregnane-type steroidal compound, (3) primary alcohols having a residue R of heterocyclic compound selected from the group consisting of galactono-gamma-lactone, N-(2-hydroxyethyl)phthalimide, 2-(3-indole)ethanol, 2-(2-hydroxyethyl)pyridine, pyridoxine, N-(2-hydroxyethyl)morpholine, 5-hydroxymethylcytosine, cytidine, uridine, arabinocytidine, thiamine, 2-(2-hydroxyethyl)piperazine, adenosine, guanosine and cyclocytidine, and (4) secondary alcohols having a $C_3-C_{10}$ linear or branched alkyl group R which may be substituted by a substituent selected from the class consisting of halogen, amino, acetyl, hydroxyl, mono- or di-alkylamino of not more than 3 carbon atoms and phenyl, or a $C_4-C_8$ alicyclic hydrocarbon group R which may be substituted by said substituent, in the presence of phospholipase DM; and the primary or secondary alcohol derivative of phospholipid so obtained.

It has previously been known that phospholipase D catalyzes a reaction of hydrolyzing the choline base-phosphoric ester of phosphatidyl choline, a phospholipid, to yield a free base and phosphatidic acid [M. Kates: Can. J. Biochem. Physiol., 32, 571 (1954)].

It was reported that when a phospholipid such as lecithin is reacted with ethanol in the presence of phospholipase D, the ester linkage between the phosphatidic acid structural moiety of the phospholipid and its alcohol structural moiety is hydrolyzed and simultaneously by the action of the enzyme to transfer the phosphatidyl group, phosphatidyl ethanol is formed [R. M. C. Dawson: Biochem. J., 102, 205 (1967), and S. F. Yang: J. Biol. Chem., 242, 477 (1967)].

Much research work has been undertaken in this field since the action of phospholipase D to transfer the phosphatidyl group as mentioned above became known. For example, British Pat. No. 1,581,810 (corresponding to West German OLS No. 2717547) discloses a primary alcohol transferring reaction between a specified phospholipid represented by the general formula in the above patent document and a primary alcohol having a linear or branched alkyl group with up to 5 carbon atoms which may be substituted by hydroxyl, halogen, amino or another substituent, utilizing the enzymatic action of phospholipase D derived from cabbage. The cited patent document states that this reaction takes place only with primary alcohols containing not more than 5 carbon atoms, and with a primary alcohol having more than 5 carbon atoms, the main product of the reaction is the corresponding phosphatidic acid. The British Patent also describes that the selection of the alcohol component is not particularly restricted so long as it is a primary alcohol meeting the above requirement.

S. Kovatchev and H. Eibl who are the inventors of the above-cited British Patent reported in Adv. Exp. Med. Biol., Vol. 101, 221 (1978) that in regard to the primary alcohol transferring reaction under the enzymatic action of phospholipase D, no transfer reaction was observed with alkanols having 7 to 10 carbon atoms, but a transfer reaction to an extent of 20% occurred with hexanol ($C_6$). On the other hand, M. M. Rokhimov reported in Uzb. Biol. Zh., vol. 3, 6–9 (1979) that no transfer reaction occurred with alcohols having at least 5 carbon atoms, for example hexanol ($C_6$).

Furthermore, R. M. C. Dawson reported that when lecithin as a phospholipid and 2-propanol as a secondary alcohol were reacted in the presence of the known cabbage-derived phospholipase D, the transfer of the phosphatidyl group of the lecithin base to the secondary alcohol did not take place [Biochem., J., vol. 102, 205 (1967)].

As stated above, it has been common technical knowledge that a transfer reaction between a phospholipid and an alcohol with the conventional phospholipase D takes place only when the alcohol is a primary alcohol, particularly a primary alcohol having a relatively small number of carbon atoms, and it does not occur at all with secondary alcohols.

The present inventors already discovered the existence of microorganisms having the ability to produce phospholipase D which differ from the known cabbage-derived phospholipase D in optimum temperature, optimum pH, etc., and disclosed them in Japanese Patent Application No. 161076/1981 (Laid-Open Patent Publication No. 63388/1983 laid open on Apr. 15, 1983), and Japanese Patent Application No. 163475/1981 (Laid-Open Patent Publication No. 67183/1983 laid open on Apr. 21, 1983).

Further investigations have led to the surprising discovery that the enzyme (to be called phospholipase DM herein) produced by the aforesaid phospholipase D-producing microorganisms catalyzes a transfer reaction between a phospholipid and a primary alcohol selected from the groups (1), (2) and (3) stated hereinabove, including primary alcohols having at least 6 carbon atoms (excepting hexanol), which have heretofore been considered incapable of forming phospholipid-primary alcohol derivatives or which have not been described in the literature heretofore.

The present inventors also have found surprisingly that the phospholipase DM can catalyze a transfer reaction between a wide range of phospholipids and secondary alcohols, in spite of the fact that it has previously been considered impossible to form phospholipid-secondary alcohol derivatives.

Investigations of the present inventors have shown that there exists an enzyme called phospholipase DM in the present invention which catalyzes the formation of a phospholipid-primary alcohol derivative from a phospholipid and, for example, geraniol, a $C_{10}$ primary alcohol, and that by reacting the phospholipid represented by formula (II) given hereinabove with the primary alcohol selected from the group consisting of (1), (2) and (3), new derivatives including phospholipid primary alcohol derivatives which have hitherto been considered impossible of formation can be produced.

The present inventors have further found that the phospholipase DM also catalyzes the formation of a phospholipid-secondary alcohol derivative from a phospholipid and, for example, 2-butanol, a $C_4$ secondary alcohol, and that by reacting the phospholipid of formula (II) with the secondary alcohol shown in (4) above in the presence of the phospholipase DM, new derivatives, including phospholipid-secondary alcohol derivatives, which have heretofore been considered impossible of formation, can be produced.

It has been found as a result of the present inventors' investigations that primary or secondary alcohol derivatives of phospholipids can be produced in good yields by an enzymatic technique under mild conditions and by easy means without the need for complex and disadvantageous chemical synthesizing means and without a likelihood of side reactions.

It is an object of this invention therefore to provide new primary or secondary alcohol derivatives of phospholipids and a process for production thereof.

The above and other objects and advantages of this invention will become more apparent from the following description.

The starting phospholipid used in the process of this invention is represented by the following formula (II).

(II)

In the above formula, A is a moiety represented by the following formula (i)

(i)

or the following formula (ii)

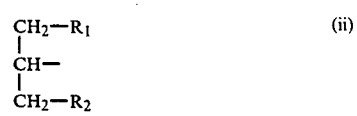

(ii)

in which $R_1$ and $R_2$ both represent —O—COR$_{11}$ or —O—R$_{12}$, or $R_1$ and $R_2$ in formula (i) together represent

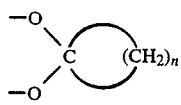

in which n represents a number of from 11 to 19, and $R_{11}$ and $R_{12}$ are identical or different and each represents a saturated or unsaturated aliphatic hydrocarbon group having 7 to 21 carbon atoms, and
B represents the group $+CH_2)_2N^+(CH_3)_3$, $+CH_2)_2NH_2$, —CH$_2$CH(NH$_2$)COOH, —CH$_2$CH$_2$NH(CH$_3$), —CH$_2$CH$_2$N(CH$_3$)$_2$, —CH$_2$CHOHCH$_2$OH or $+CH_2)_mH$ in which m represents a number of from 1 to 5.

The starting phospholipids of formula (II) are known compounds and are available on the market. They can be extracted from naturally occurring materials, or synthesized, by methods known per se. For example, lecithin, cephalin, phosphatidyl serine, phosphatidyl N-methylethanolamine, phosphatidyl N,N-dimethylethanolamine, phosphatidyl glycerol, and alkyl esters of phosphatidic acid which can be extracted from animal and vegetable tissues by known means, either singly or in combination, can be used directly or after purification. Alkyl ether-type phospholipids or beta-type phospholipids can also be utilized by chemically synthesizing a part or the whole of their structures by known methods.

The primary alcohol to be reacted with the starting phospholipid of formula (II) in this invention in the presence of phospholipase DM is at least one member selected from the group consisting of (1), (2) and (3) above. The secondary alcohol to be so reacted is at least one member of the group shown in (4) above.

Examples of the primary alcohols of group (1) include aliphatic alcohols having no substituent, such as 1-heptanol (C$_7$), 1-octanol (C$_8$), 2-ethyl-1-hexanol (C$_8$), 1-nonanol (C$_9$), 1-decanol (C$_{10}$), 1-undecanol (C$_{11}$), 1-dodecanol (C$_{12}$), 1-tetradecanol (C$_{14}$), 1-hexadecanol (C$_{16}$), 1-octadecanol (C$_{18}$), 1-docosanol (C$_{20}$), 1-eicosanol (C$_{22}$), 1-hexacosanol (C$_{26}$) geraniol (C$_{10}$), citronellol (C$_{10}$), farnesol (C$_{15}$) and phytol (C$_{20}$); polyhydric aliiphatic alcohols such as 1,6-hexanediol (C$_6$), 1,2,6-hexanetriol (C$_6$), sorbitol (C$_6$), mannitol (C$_6$), 2-n-butyl-2-ethyl-1,3-propanediol (C$_9$), 2-ethyl-1,3-hexanediol (C$_8$), 1,1,1-tris(hydroxymethyl)propane (C$_6$), 3,3-bis(hydroxymethyl)heptane (C$_9$), 1,10-decanediol (C$_{10}$), 1,12-dodecanediol (C$_{12}$), trimethylol propane and dipentaerythritol; aliphatic alcohols having an amino group, such as 6-amino-1-hexanol (C$_6$), triethanolamine (C$_6$), N-butyldiethanolamine (C$_8$), serine ethyl ester, dihydroxyethylglycine (C$_6$), sphingosine (C$_{18}$), N-methyl pentanolamine, N-methyl hexanolamine, N-ethyl butanolamine, N-ethyl pentanolamine, N-ethyl hexanolamine, N-propyl propanolamine, N-propyl butanolamine, N-propyl pentanolamine, N-propyl hexanolamine, N-butyl ethanolamine, N-butyl propanolamine, N-butyl butanolamine, N-butyl pentanolamine, N-butyl hexanolamine, N-pentyl ethanolamine, N-hexyl ethanolamine, N,N-dimethyl butanolamine, N,N-dimethyl pentanolamine, N,N-dimethyl hexanolamine, N,N-diethyl ethanolamine, N,N-diethyl propanolamine, N,N-diethyl butanolamine, N,N-diethyl pentanolamine, N,N-diethyl hexanolamine, N,N-dipropyl ethanolamine, N,N-dipropyl propanolamine, N,N-dipropyl butanolamine, N,N-dipropyl pentanolamine, N,N-dipropyl hexanolamine, N,N-dibutyl propanolamine, N,N-dibutyl butanolamine, N,N-dibutyl pentanolamine, N,N-dibutyl hexanolamine, N,N-dipentyl ethanolamine, N,N-dihexyl ethanolamine, N,N,N-trimethyl propanolamine, N,N,N-trimethyl butanolamine, N,N,N-trimethyl pentanolamine, N,N,N-trimethyl hexanolamine, N,N,N-triethyl ethanolamine, N,N,N-triethyl propanolamine, N,N,N-triethyl butanolamine, N,N,N-triethyl pentanolamine, N,N,N-triethyl hexanolamine, N,N,N-tripropyl ethanolamine, N,N,N-tripropyl propanolamine, N,N,N-tripropyl butanolamine, N,N,N-tripropyl pentanolamine, N,N,N-tripropyl hexanolamine, N,N,N-tributyl ethanolamine, N,N,N-tributyl propanolamine, N,N,N-tributyl butanolamine, N,N,N-tributyl pentanolamine, N,N,N-tributyl hexanolamine, N,N,N-tripentyl ethanolamine, N,N,N-trihexyl ethanolamine, N,N-dibutyl ethanolamine, and N-(3-aminopropyl)diethanolamine; aliphatic alcohols having a carboxyl group, such as 16-hydroxyhexadecanoic acid (C$_{16}$) and gluconic acid (C$_6$); aliphatic alcohols having an ester linkage, such as monolaurin (C$_{15}$), monoolein (C$_{21}$), 1,2-dilaurin (C$_{27}$), 1,2-distearin (C$_{30}$), 2-hydroxyethyl methacrylate (C$_6$), ethylene glycol monolaurate, diethylene glycol monolaurate, ethylene glycol monostearate, diethylene glycol monostearate, ethylene glycol monooleate, diethylene glycol monooleate, ethylene glycol monopalmitate, and diethylene glycol monopalmitate; aliphatic alcohols having an amide linkage, such as pantothenyl alcohol (C$_9$), pantetheine (C$_{11}$), tri-L-serine, L-seryl-L-leucine, L-seryl-L-methionine, L-seryl-L-arginine, L-seryl-L-lysine, L-seryl-L-glutamine, N-capriloyl ethanolamine, N-caproyl ethanolamine, N-lauroyl ethanolamine, N-myristoyl ethanolamine, N-palmitoyl ethanolamine, N-stearoyl ethanolamine, N-oleoyl ethanolamine, N-palmitoleoyl ethanolamine, N-linoloyl ethanolamine, N-linolenoyl ethanolamine, N-arachidonoyl ethanolamine, N-eicosanoyl ethanolamine, N-docosanoyl ethanolamine, L-seryl-L-histidine, and L-seryl-L-tryptophan; aliphatic alcohols having an ether linkage, such as triethylene glycol (C$_6$), diethylene glycol monobutyl ether (C$_8$); ethylene glycol monolauryl ether, diethylene glycol monolauryl ether, ethylene glycol monocetyl ether, diethylene glycol monocetyl ether, ethylene glycol monostearyl ether, diethylene glycol monostearyl ether, ethylene glycol monooleyl ether, diethylene glycol monooleyl ether, ethylene glycol monobutyl ether, ethylene glycol mono(2-diethylaminoethyl) ether, ethylene glycol monohexyl ether, ethylene glycol monotolyl ether, diethylene glycol monoethyl ether, diethylene glycol monohexyl ether, tetraethylene glycol, pentaethylene glycol, hexaethylene glycol, octaethylene glycol, decaethylene glycol, and dodecaethylene glycol; unsubstituted aromatic alcohols such as benzyl alcohol (C$_7$), beta-phenethyl alcohol (C$_8$), 3-phenyl-1-propanol (C$_9$), cinnamyl alcohol (C$_9$), L-seryl-L-tyrosine, L-seryl-L-phenylalanine, L-serine benzyl ester, L-serine beta-naphthylamide, N-dinitrophenyl-L-serine, N-(1-dimethylaminonaphthalene-5-sulfonyl)-L-serine, ethylene glycol monobenzyl ether, ethylene glycol monooctylphenol ether, diethylene glycol monooctylphenol ether, ethylene glycol monononylphenol ether, and diethylene glycol monononylphenol ether; aromatic alcohols having a substituent, such as p-chlorobenzyl alcohol (C$_7$), p-aminophenethyl alcohol ($C_8$), N-ethyl-N-(2-hydroxyethyl)-m-toluidine ($C_{11}$), beta-hydroxyethylaniline ($C_8$), N-(2-cyanoethyl)-N-(2-hydroxyethyl)-aniline ($C_{11}$), N-phenyldiethanolamine ($C_{10}$), anisic alcohol ($C_8$), 1,4-di(2-hydroxyethoxy)benzene ($C_{10}$), ethylene glycol monophenyl ether ($C_8$), mephenesin ($C_{10}$), 2-hydroxyethylsalicylic acid ($C_9$), ethylene glycol monochlorophenyl ether and 6-chlorohexanol; polycylic compounds such as O,O-bis(2-hydroxyethyl)tetrabromobisphenol ($C_{19}$) and 2-naphthalene ethanol ($C_{12}$); and alicyclic alcohols such as retinol ($C_{20}$) and 1,4-dihydroxymethyl cyclohexane ($C_8$).

Examples of the primary alcohols of group (2) include aldosterone, corticosterone, cortisone, dehydrocorticosterone, deoxycorticosterone, hydrocortisone, prednisolone, prednisone, tetrahydrocortisol, tetrahydrocortisone and triamcinolone.

Examples of the primary alcohols of group (3) include galactono-gamma-lactone, N-(2-hydroxyethyl)phthalimide, 2-(3-indole)ethanol, 2-(2-hydroxyethyl)pyridine, pyridoxine, pyridoxal, pyridoxamine, N-(2-hydroxyethyl)morpholine, 5-hydroxymethylcytosine, cytidine, uridine, arabinocytidine, adenosine, guanosine, cyclocytidine, adenine deoxyriboside, cytosine deoxyriboside, guamine deoxyriboside, 5-hydroxymethyluracil, thymine deoxyriboside, uracil deoxyriboside, inosine, orotidine, 2-(2-hydroxyethyl)piperazine, thiamine and toxopyrimidine.

Examples of the secondary alcohols of group (4) include secondary aliphatic alcohols such as 2-propanol, 2-butanol, 2-pentanol, 3-pentanol, 4-methyl-2-pentanol, 2-hexanol, 3-hexanol, 1-hexen-3-ol, 2-heptanol, 3-heptanol, 2-octanol, 2-nonanol, 3-nonanol, 2-decanol, 3-decanol, 2,3-butanediol, 2-methyl-2,4-pentanediol, 1-chloro-2-propanol, 1-bromo-2-butanol, 1-amino-2-propanol, diisopropanolamine, 1-amino-2-butanol, 3-hydroxy-2-butanone, ethyl lactate, beta-hydroxybutyric acid and dipropylene glycol; aromatic secondary alcohols such as 1-phenylethanol, 1-phenyl-2-propanol, p-chlorophenylmethylcarbinol, alpha-(1-aminoethyl)-p-hydroxybenzyl alcohol and diphenyl methanol; and alicyclic secondary alcohols such as cyclobutanol, cyclopentanol, cyclohexanol, cyclooctanol, 2-chlorocyclohexanol and 1,4-dihydroxycyclohexane.

The primary or secondary alcohols in groups (1) to (4) may be naturally occurring or synthetic materials. Preferably, they are used after purification by a suitable known means so as to minimize inclusion of other alcohols. The purifying means may, for example, be distillation, recrystallization, column chromatography on alumina, silica gel, activated carbon, ion-exchange resins, etc., thin-layer chromatography, and suitable combinations of these purifying means.

According to the process of this invention, the phospholipid of formula (II) is reacted with the primary or secondary alcohol selected from the group consisting of (1) to (4) in the presence of phospholipase DM.

The phospholipase DM used at this time may, for example, be a phospholipase DM which is produced by a phospholipase DM-producing microorganism. The phospholipase DM can be distinguished from the known phospholipase D extracted from cabbage in that the latter has an optimum temperature of not more than 40° C. and an optimum of 5.4 to 5.6, whereas the former has an optimum temperature of 60° to 70° C. and an optimum pH of about 7. The phospholipase DM can also be distinguished from the known phospholipase D in that it catalyzes not only the formation of a phospholipid-primary alcohol derivative from geraniol, a $C_{10}$ primary alcohol, and the phospholipid of formula (II), such as lecithin, and the formation of a phospholipid-secondary alcohol derivative from 2-butanol, a $C_4$ secondary alcohol, and the phospholipid of formula (II), such as lecithin.

Examples of the phospholipase DM-producing microorganism are those belonging to the genus Nocardiopsis, such as Nocardiopsis sp. No. 779 (FERM-P No. 6133; international deposit number BP 512 under the Budapest Treaty), disclosed in the above-cited Japanese Patent Application No. 161076/1981 (Laid-Open Patent Publication No. 63388/1983 laid open on Apr. 15, 1983), and those belonging to the genus Actinomadura, such as Actinomadura sp. No. 362 (FERM-P No. 6132; international deposit number BP 511 under the Budapest Treaty) which are disclosed in Japanese Patent Publication No. 163475/1981 (Laid-Open Patent Publication No. 67183/1983 laid open on Apr. 21, 1983). Table 1 below summarizes the differences in enzymological properties between the phospholipases DM used in the process of this invention and the known phospholipase D.

TABLE 1

|  | Phospholipase DM from the Actinomadura strain | Phospholipase DM from the Nocardiopsis strain | Known phospholipoase D from cabbage |
| --- | --- | --- | --- |
| Optimum temperature (°C.) | 60–70 | 60–70 | below 40 |
| Optimum pH | About 7 | About 7 | 5.4–5.6 |
| Activators | Nonionic surfactants such as Triton X-100, deoxychloic acid Cholic acid, $Ca^{++}$, diethyl ether, and albumin | Nonionic surfactants such as Triton X-100, diethyl ether, and $Ca^{++}$ | Anionic surfactants such as sodium dodecylsulfate, deoxycholic acid, phosphatidic acid, $Ca^{++}$, diethyl ether |
| Inhibitors | Cetyl pyridinium chloride | Sodium dodecylsulfate, and cetyl pyridinium chloride | EDTA, cationic surfactnts, choline, ethanolamine, and p-chloromercury benzoate |
| Phosphatidyl transferase activity | Transfer to primary aliphatic, aromatic, alicyclic and heterocyclic alcohols having 1 to 26 carbon atoms, saccharides such as pentose and hexose, and some secondary alcohols | Same as the left. | Transfer to primary aliphatic alcohols having 1 to 6 carbon atoms is effected. No transfer to saccharides such as pentose and hexose and secondary alcohols. |

TABLE 1-continued

| | Phospholipase DM from the Actinomadura strain | Phospholipase DM from the Nocardiopsis strain | Known phospholipoase D from cabbage |
|---|---|---|---|
| | is effected. | | |
| Catalytic action on the formation of phospholipid-primary alcohol derivatives between $C_{10}$ primary alcohol (geraniol) and phospholipid (lecithin) | Yes | Yes | No |
| Catalytic action on the formation of phospholipid-secondary alcohol derivatives between $C_4$ secondary alcohol (2-butanol) and phospholipid (lecithin) | Yes | Yes | No |

Presumably, it is due to the aforesaid differences in enzymological properties between the known phospholipase D and the phosholipases DM used in the process of this invention that phospholipid-primary or secondary alcohol derivatives which cannot be obtained by using the known phospholipase D can be produced by the process of this invention. It should be understood however that this presumption does not in any way limit the process of this invention.

The microbiological properties of Nocardiopsis sp. No. 779 (FERM-P No. 6133; BP 512) and Actinomadura sp. No. 362 (FERM-P No. 6132; BP 511) which have the ability to produce phospholipase DM and can be utilized in the process of this invention, the method of measuring the potencies of the phospholipases DM produced by these microorganism strains and their physico-chemical properties are described below.

Microbiological properties of Nocardiopsis sp. No. 779 (FERM-P No. 6133; BP 512)

(a) Morphology

Growth good on glucose-asparagine-agar, glycerol-asparagine-agar, and yeast-malt-agar media, and moderate in a starch-inorganic salt-agar medium, forming colonies of aerial mycelia.

The color of the colonies having spores formed therein changes slightly with the type of the culture medium and the time of observation, but is generally white to grayish white to bright gray.

Aerial mycelia do not form, or grow poorly, on sucrose-nitrate-agar, nutrient agar and oatmeal-agar media.

Microscopic observation of this strain grown on an agar medium shows that the aerial hyphae are 0.5 to 0.8 micron in diameter and are long and straight with many branches, and sometimes gently wavy or flexuous. The entire aerial mycelia are formed of chains all composed of about 10 to 100 more more spores.

The spores are 0.5–0.8×0.5×1.6 micron long, and nearly of a short cylindrical shape, and their sizes are slightly irregular.

Substrate hyphae are 0.4 to 0.7 micron in diameter, and stretch with branches. They do not always fragment on an agar medium, but when cultivated in a liquid culture medium, they fragment into small fragments in almost all cases.

Flagellated spores, sporangia, sclerotia, etc., are not formed, however.

(b) Characteristics on various media

The following experiments were carried out mainly in accordance with the methods of E. B. Shirling (Int. J. Syst. Bacteriol., vol. 16, pages 313–340, 1966).

The colors of the mycelia were determined by using "Standards of Colors" (Japanese Institute of Colors, 1964), and are described with a parenthesized symbolic or numerical indication of the color, saturation, and brightness in this order.

The cultivation was carried out at 25° C., and the results of observation on various media in the second to third weeks when the growth was most vigorous are summarized below. In the following description, the colors of the surfaces of substrate mycelia given under the headline "growth" are those observed after the lapse of one week from the initiation of cultivation which was before the formation of spores. No result is given where the evaluation of colors on the surfaces of substrate mycelia was difficult because of the early formation of spores.

Sucrose-nitrate-agar medium

Growth: Thin and poor. Colorless.
Color of substrate mycelium: Grayish white (19).
Aerial mycelium: Slightly formed. Colorless.
Soluble pigment: None.

Glucose-asparagine-agar medium

Growth: Good. Yellowish white (Y-1-19).
Color of substrate mycelium: Yellowish gray (rY-2-19).
Aerial mycelium: Abundant in cottony form. Light brownish gray (rO-1-17).
Soluble pigment None.

Glycerol-asparagine-agar medium

Growth: Good.
Color of substrate mycelium: Pale yellow (rY-3-19).
Aerial mycelium: Formed thinly in cottony form. Light gray (18).
Soluble pigment: None.

Starch-inorganic salt-agar medium

Growth: Good. Yellowish gray (Y-1-19).
Color of substrate mycelium: Yellowish gray (rY-1-19).
Aerial mycelium: Moderate, powdery. Grayish white (19).
Soluble pigment: None.

Tyrosine-agar medium

Growth: Good. Yellowish brown (YO-3-16).
Color of substrate mycelium: Light brown (0-3-15).
Aerial mycelium: Good to excellent. Light gray (18).
Soluble pigment: Brown melanoid pigment produced.

Nutrient agar medium

Growth: Poor. Colorless.
Color of substrate mycelium: Brownish white (YO-1-19).
Aerial mycelium: Not formed.
Soluble pigment: None.

Yeast-malt-agar medium

Growth: Good.
Color of substrate mycelium: Dull yellow orange (YO-4-18).
Aerial mycelium: Good to excellent. Grayish white (19).
Soluble pigment: Brown melanoid pigment produced.

Oatmeal-agar medium

Growth: Moderate. Yellowish gray (Y-1-19).
Color of substrate mycelium: Yellowish gray (Y-1-19).
Aerial mycelium: Poor. White (20).
Soluble pigment: None.

(c) Physiological properties
1. Growth temperature
Grows at about 5° to 30° C., and best at 20° to 30°.
2. Liquefaction of gelatin
Negative (when cultivated on a glucose-peptone-gelatin medium at 25° C. for 3 weeks).
3. Hydrolysis of starch
Positive (when cultivated on a starch-agar medium at 25° C. for 3 to 4 weeks).
4. Coagulation and peptonization of skimmed milk
Both negative (when cultivated at 30° C. for 3 to to 4 weeks).
5. Formation of a melanoid pigment
Positive on peptone-yeast-iron-agar and tyrosine-agar media (at 25° C. for 2 to 4 days).

(d) Utilization of carbon sources (when cultivated at 30° C. for 10 to 16 days)
L-arabinose: —
Sucrose: —
D-xylose: —
Inositol: —
D-glucose: +
L-rhamnose: —
D-fructose: —
Raffinose: —

(e) Chemical analysis of cells
2,6-Diaminopimelic acid of this strain has the meso-form of DAP in hydrolysates of whole organisms, and does not contain hydroxydiaminopimelic acid. The sugar pattern of the cell walls of this strain is such that it lacks arabinose, xylose, madurose, rhamnose, but contains galactose and mannose. The present strain does not contain nocardomycolic acid.

The foregoing analytical results are evaluated in accordance with the classification methods described in Bergey's Manual of the Determinative Bacteriology, 8th edition, pages 657-658 (1974), M. P. Lechevalier and H. A. Lechevalier, "Inter. J. System. Bacteriol., vol. 20, pages 435-443, 1970, and J. Meyer, Int. J. Syst. Bacteriol., vol. 26, pages 487-493, 1976. It was found that the cell wall type of the present strain is type III, and its cell wall sugar pattern is type C.

Because the present strain has cell wall type III and cell wall sugar pattern C, the Lechevalier's classification method shows it to belong to either of the genera Geodermatophilus, Actinobifida, Thermoactinomyces and Actinomadura of the dassonvillei type.

Since, however, the present strain has such morphological characteristics that all of the aerial mycelia are composed of long chains of spores, the substrate mycelia are finely fragmented, but no endospores, flagellated spores norsporangia are found in it, it is reasonable to identify this strain as belonging to the genus Actimomadura of the dassonvilleic type. It is noted in this regard that the genus Actinomadura of the dassonvillei type has recently been unified into the new genus Nocardiopsis advocated by J. Meyer, and is generally dealt with by the name of genus Nocardiopsis.

Thus, the present strain was named Nocardiopsis sp. No. 779. It was deposited in Fermentation Research Institute of the Agency of Industrial Science and Technology, Japan under the deposit number "FERM-P No. 6133 (the international deposit number BP 512)".

In the present invention, not only Nocardiopsis sp. No. 779 and its mutant strains, but also all other strains belonging to the genus Nocardiopsis (the former genus Actinomadura of the dassonvillei type) and capable of producing phospholipase DM can be used to produce phospholipase DM.

Microbiological properties of Actinomadura sp. No. 362 (FERM-P No. 6132; the international deposit number BP 511):

(a) Morphology

Growth good on starch-inorganic salt-agar, tyrosine-agar, yeast-malt-agar, and oatmeal-agar media, but moderate on a glycerol-asparagine-agar medium, forming colonies of aerial mycelia.

The color of the colonies having spores formed therein varies slightly with the type of the culture medium and the time of observation, but generally it is slightly purplish grayish white to gray.

Aerial hyphae are not formed, or formed only poorly, on sucrose-nitrate-agar, nutrient agar and glucose-asparagine-agar media.

Microscopic observation of the present strain grown on an agar medium shows that the aerial mycelia are branched with a width of 0.7 to 0.8 microns, partly form loops or helical filaments, and are mainly straight with some flexuous parts, and their tips are mostly wound in loop form.

Spores are formed in 10 to 100 or more chains, and constitute almost the entire aerial mycelia.

The size of the spores is 0.7-0.8×0.7-1.6 microns, and their shape is short-cylindrical. Both their size and shape are slightly irregular.

The substrate mycelia are 0.4 to 0.7 micron wide, and stretch flexuously with irregular branches. No flagellated spores, sporangia nor sclerotia are formed.

Flagmentation of the septa and mycelia is not observed. (But sometimes, fragmentation of the mycelia occurs in liquid culture.)

(b) Characteristics on various culture media

The following experiments were carried out mainly in accordance with the methods of E. B. Shirling (Int. J. Syst. Bacteriol., vol. 16, pages 313-340, 1066).

The colors of mycelia were determined by using "Standards of Colors" (Japanese Institute of Colors, 1964), and are described with a parenthesized symbolic or numerical indication of the color, saturation, and brightness in this order.

The cultivation was carried out at 25° C., and the results of observation on various media in the second to third weeks when the growth was most vigorous are summarized below. In the following description, the colors of the surfaces of substrate mycelia given under the headline "growth" are those observed after one week from the initiation of cultivation which was before the formation of spores. No result is given where the evaluation of colors on the surfaces of substrate mycelia was difficult because of the early formation of spores.

Sucrose-nitrate-agar medium

Growth: Poor. Grayish white (19).
Color of substrate mycelium: Grayish white (19).
Aerial mycelium: Formed moderately in powder form. Grayish white (19).
Soluble pigment: None.

Glucose-asparagine-agar medium

Growth: Good. Yellowish white (Y-1-19).
Color of substrate mycelium: Light olive gray (Y-1-18).
Aerial mycelium: Formed poorly. Light brownish gray (YO-1-19).
Soluble pigment: None.

Glycerol-asparagine-agar medium

Growth: Moderate. Greenish white (gY-1-19).
Color of substrate mycelium: Pale yellowish brown (rY-2-18).
Aerial mycelium: Formed thickly in powder form. Light gray (18).
Soluble pigment: None.

Starch-inorganic salt-agar medium

Growth: Good. Yellowish gray (Y-1-19).
Color of substrate mycelium: Yellowish gray (Y-1-19).
Aerial mycelium: Good. Pale orange (O-2-19).
Soluble pigment: None.

Tyrosine-agar medium

Growth: Good. Pale yellowish brown (YO-2-18).
Color of substrate mycelium: Pale brown (YO-3-17).
Aerial mycelium: Good to excellent. Brownish white (O-1-19).
Soluble pigment: Brown melanoid pigment produced.

Nutrient agar medium

Growth: Thin and poor. Colorless.
Color of substrate mycelium: Brownish white (YO-1-19).
Aerial mycelium: Not formed.
Soluble pigment: Brown melanoid pigment produced.

Yeast-malt-agar medium

Growth: Good.
Color of substrate mycelium Dull yellow (rY-4-18).
Aerial mycelium: Good to excellent. Light purplish gray (pR-1-17).
Soluble pigment: None.

Oatmeal-agar medium

Growth: Good. Yellowish gray (rY-1-19).
Color of substrate mycelium: Yellowish gray (rY-1-19).
Aerial mycelium: Good to excellent. Brownish white (YO-1-19).
Soluble pigment: None.

(c) Physiological properties

1. Growth temperature

Grows at about 10° to 37° C., and best at 20° to 30° C.

2. Liquefaction of gelatin

Negative (on a glucose-peptone-gelatin medium at 25° C. for 3 weeks).

3. Hydrolysis of starch

Positive (on a starch-agar medium at 25° C. for 3 weeks).

4. Coagulation and peptonization of skimmed milk

Not coagulated but peptonized (at 30° C. for 3 to 4 weeks).

5. Formation of a melanoid pigment

Positive on peptone-yeast-iron-agar and tyrosine-agar media (at 25° C. for 2 to 4 days).

(d) Utilization of carbon sources (at 30° C. for 10 to 16 days)

L-arabinose: +
Sucrose: −
D-xylose: +
Inositol: ±
D-glucose: +
L-rhamnose: −
D-fructose: −
Raffinose: −

(e) Chemical analysis of cells 2,6-Diaminopimelic acid of this strain is of the meso-type. The sugar composition of the whole cell walls is such that it does not contain arabinose, xylose, rhamnose, but contains madurose, galactose and mannose.

The foregoing analytical results are evaluated in accordance with the classification methods described in Bergey's Manual of the Determinative Bacteriology, 8th edition, pages 657-658 (1974), and M. P. Lechevalier and H. A. Lechevalier, "Inter. J. System. Bacteriol., vol. 20, pages 435-443, 1970". It was found that the cell wall type of the present strain is type III, and its cell wall sugar pattern is type B.

Because the present strain has cell wall type III and cell wall sugar pattern B, it belongs to either of the genera Microbispora, Streptosporangium, Spirillospora, Planomonospora, Dermatophilus, and Actinomadura.

Since, however, the present strain has such morphological characteristics that spore chains composed of many spores are formed, and no sclerotia, flagellated spores nor sporangia are found in it, it is taxonomically reasonable to identify this strain as belonging to the genus Actimomadura.

Thus, the present strain was named Actinomadura sp. No. 362. It was deposited in Fermentation Research Institute of the Agency of Industrial Science and Technology, Japan under the deposit number "FERM-P No. 6132 (the international deposit number BP 511)".

In the present invention, not only Actinomadura sp. No. 362 and its mutant strains, but also all other strains belonging to the genus Actinomadura and capable of producing phospholipase DM can be used to produce phospholipase DM.

The phospholipase DM utilized in the process of this invention is produced by cultivating the phospholipase DM-producing strain exemplified above in a culture medium, and collecting phospholipase DM from the culture broth. The cultivation can be carried out in a liquid culture or solid culture mode, but industrially, a submerged culture mode is advantageous.

Carbon sources, nitrogen sources, inorganic salts and traces of other nutrients which are generally used in microbial cultivation may be used in this invention as cultivation sources. Other nutrient sources which phospholipase DM-producing microorganisms of the genus Nocardiopsis or Actinomadura can utilize may also be used in this invention.

Examples of the carbon sources include glucose, fructose, sucrose, lactose, starch, glycerol, dextrin, molasses, sorbitol, fatty acids, oils and fats, crude lecithin, alcohols and organic acids. They may be used either singly or in combination.

The nitrogen sources may be inorganic or organic. Examples of the inorganic nitrogen sources include ammonium nitrate, ammonium sulfate, urea, sodium nitrate, ammonium phosphate monobasic, ammonium phosphate dibasic and ammonium chloride. Examples of the organic nitrogen sources include flours, brans and oil extraction residues of soybean, rice, corn, cotton seed, rape seed and wheat, corn steep liquor, peptone, yeast extract, meat extract, casein and amino acids.

Examples of the inorganic salts and trace nutrients include salts of phosphoric acid, magnesium, potassium, iron, aluminum, calcium, manganese and zinc, vitamins, nonionic surface-active agents and defoamers. Such substances promote the growth of the microorganisms or the production of phospholipase DM, and may be used as required.

The cultivation is carried out under aerobic conditions. The cultivation may be properly selected and varied within a range of temperatures at which the microorganism strain grows well and produces phospholipase DM. Temperatures of about 20° to about 35° C. are especially preferred.

The cultivation time varies depending upon the cultivating conditions. The cultivation may be performed until the amount of the phospholipase DM produced reaches a maximum. In the case of liquid culture, for example, it is about 1 to 3 days.

The phospholipase DM produced in the culture broth is mainly dissolved in it. Hence, the phospholipase DM can be collected from the culture broth after removing solid materials from it by filtration.

In collecting the phospholipase DM from the filtrate, all methods usually employed for enzyme preparation can be utilized. The methods include, for example, salting out with ammonium sulfate, sodium chloride, etc., precipitation with organic solvents such as acetone, ethanol and methanol, dialysis, ion-exchange chromatography, adsorption chromatography, gel filtration, adsorption on adsorbents, and isoelectric precipitation. These methods may be combined if the combined use increases the effect of purifying phospholipase DM.

The phospholipase DM may be obtained in the form of a liquid or solid by, for example, adding various salts, sugars, proteins, lipids and surface-active agents as stabilizers, or by concentrating it under pressure, drying it under reduced pressure or lyophilizing it without adding such stabilizers.

The enzyme activity of the phospholipase DM utilized in the process of this invention is determined by measuring the amount of a base which is formed when the phospholipase DM acts on the substrate glycerophospholipid to decompose the ester linkage between phosphoric acid and the nitrogen-containing base. Unless otherwise indicated, the activity of phospholipase DM is measured by the choline oxidase method to be described hereinafter.

Method of measuring the activity of an enzyme:

Distilled water (0.15 ml), 0.1 ml of 0.2M Tris-HCl buffer (pH 7.2) and 0.05 ml of 0.1M aqueous calcium chloride solution are mixed with 0.1 ml of 1% emulsion of purified lecithin from egg yolk (an emulsion of 0.1 g of lecithin, 1 ml of ethyl ether and 10 ml of distilled water obtained by ultrasonication). To the mixture is added 0.1 ml of an enzyme solution and reacted at 37° C. for 20 minutes. Then, 0.2 ml of 1M Tris-HCl buffer (pH 8.0) containing 50 mM disodium ethylenediamine tetraacetate, and immediately then, the mixture is boiled for 5 minutes, followed by completely stopping the reaction. Then, 4 ml of a solution obtained by dissolving a choline color-forming agent contained in a kit of a reagent for choline esterase measurement (produced by Nippon Shoji Co., Ltd.) in a color dissolving liquid is added, and reacted at 37° C. for 20 minutes. Then, the absorbance of the reaction solution at 500 nm is measured.

As a control, the absorbance of the product obtained by the same procedure as above except that an enzyme solution previously deactivated by heat is used.

The activity of the enzyme to liberate 1 micromole of choline per minute is defined as one unit.

The physico-chemical properties of phospholipases DM produced and purified by the method shown below in section 9 (Method of purification) using Nocardiopsis sp. No. 779 and Actinomadura sp. No. 362 are described below.

1. Activity

These phospholipases DM decomposes the ester linkage of phosphoric acid and a nitrogen-containing base in a glycerophospholipid to liberate the base and phosphatidic acid.

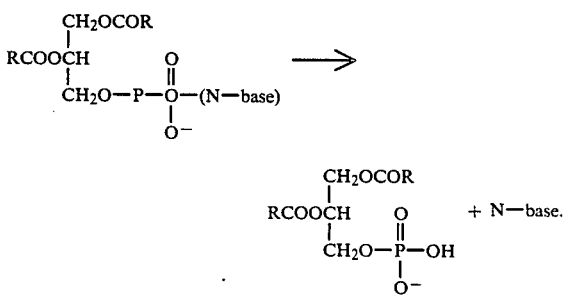

2. Substrate specificity

The same reaction as in the aforesaid method of measuring the activity of the enzyme was carried out except that 0.1 ml of an emulsion containing 0.5 micromole of each of lecithin, lysolecithin and sphingomyelin is used as a substrate and an aqueous solution containing 1% of Triton X-100 is used instead of distilled water. The amount of choline liberated as a result of the reaction is measured, and the activity of phospholipase DM on the substrate is measured. It was found that when the activity of the enzyme on lecithin is taken as 100, the relative activity of phospholipase DM derived from the Nocardiopsis strain is 4.9 on lysolecithin and 0.3 on sphingomyelin, and the relative activity of phospholipase DM derived from the Actinomadura strain is 3.6 on lysolecithin and 0.3 on sphingolyelin.

3. Optimum pH

The activity of phospholipase DM is measured by using a formic acid-sodium formate buffer at a pH of 3.0 to 4.0, an acetic acid-sodium acetate buffer at a pH of 4.0 to 5.5, a Tris-maleic acid-sodium hydroxide buffer at a pH of 5.5 to 8.5, a Tris-HCl buffer at a pH of 7.0 to 9.0, and a glycine-sodium hydroxide buffer at a pH of 9.0 to 10.0 instead of the buffer used in the method of measuring the activity of the enzyme. The optimum pH is thus measured. The optimum pH is also measured when 0.15 ml of a 1% aqueous solution of Triton X-100 (a reagent made by Wako Pure Chemicals Co., Ltd.) is used instead of 0.15 ml of distilled water.

It is found that when distilled water is used, the optimum pH of phospholipase DM from the Nocardiopsis strain is about 7 (6.5–7.0), and the optimum pH of phospholipase DM derived from the Actinomadura strain is about 7; and that when the 1% aqueous solution of Triton X-100 is used, the optimum pH of phospholipase DM derived from the Nocardiopsis strain is about 5, and the optimum pH of phospholipase DM derived from the Actinomadura strain is about 5.5.

4. Optimum temperature

The activity of the enzyme is measured by the method of measuring the activity of the enzyme at reaction temperatures of 10°, 20°, 25°, 37°, 40°, 50°, 60°, 70°, 80° and 90° C. The result is that the optimum temperature of phospholipase DM derived from the Nocardiopsis strain is 60° to 80° C., especially 60° to 70° C., and the optimum temperature of phospholipase DM derived from the Actinomadura strain is 55° to 80° C., especially 60° to 70° C.

5. pH stability

To 0.1 ml of an enzyme solution is added 0.2 ml (in the case of phospholipase DM derived from the Nocardiopsis strain) or 0.9 ml (in the case of phospholipase DM derived from the Actinomadura strain) of each of various buffers (0.1M). Specifically, there were used a glycine-HCl buffer at a pH of 3.0 to 3.5, an acetic acid-sodium acetate buffer at a pH of 3.5 to 7.0, a Tris-maleic acid-sodium hydroxide buffer at a pH of 5.0 to 8.0, a Tris-HCl buffer at a pH of 7.0 to 9.0, and a glycine-sodium hydroxide buffer at a pH of 9.0 to 9.5. The mixture is maintained at 25° C. for 2 hours. Thereafter, 1.2 ml (in the case of phospholipase DM derived from the Nocardiopsis strain), or 9.0 ml (in the case of phospholipase DM derived from the Actinomadura strain) of 0.5M Tris-HCl buffer (pH 7.2) is added to the resulting enzyme buffer solution to adjust its pH to 7.0 to 7.3. The activity of the enzyme is measured by using 0.1 ml of this solution in accordance with the method of measuring the activity of the enzyme described hereinabove. The stable pH range is thus examined. It is found that phospholipase DM derived from the Nocardiopsis strain is especially stable at a pH of 4.0 to 7.0, and phospholipase DM derived from the Actinomadura strain is especially stable at a pH of 4.0 to 8.0. The stable pH range is examined by the same procedure as above except that 0.15 ml of a 1% aqueous solution of Triton X-100 is used instead of 0.15 ml of distilled water used in the method of measuring the activity of the enzyme. The results are much the same as those obtained by the aforesaid procedure.

6. Heat stability

To 0.1 ml of an enzyme solution is added 4 ml (in the case of phospholipase DM derived from the Nocardiopsis strain) or 9.9 ml (in the case of phospholipase DM derived from the Actinomadura strain) of 0.1M Tris-HCl buffer (pH 7.2), and the mixture is left to stand for 30 minutes at a temperature of 20°, 30°, 37°, 40°, 50°, 60° and 65° C. respectively. The remaining enzyme activity is then measured. It is found consequently that the activity of phospholipase DM derived from the Nocardiopsis strain is scarcely lost by heat-treatment at 30° C. for 30 minutes, and 80% of it remains after heat-treatment at 50° C. for 30 minutes and that the activity of phospholipase DM derived from the Actinomadura strain is scarcely lost by heat-treatment at 30° C. for 30 minutes, and 60% of it remains after heat-treatment at 50° C. for 30 minutes.

7. Influences of various substances

In the method of measuring the activity of the enzyme described hereinabove, 0.05 ml of an aqueous solution of each of various substances is added instead of the aqueous calcium chloride solution so that its concentration in the enzyme reaction system becomes 1 mM. The activity of the enzyme is then measured. The activity of the enzyme at the time of adding water is taken as 100, and the relative activity of the enzyme is determined. It is found that $AlCl_3$, $CuSO_4$, $ZnSO_4$, $CoCl_2$, $CaCl_2$, $FeCl_3$, $FeSO_4$, $MgCl_2$, $SnCl_2$, sodium deoxycholate, ethanol, isopropanol, t-butanol, and Triton X-100 have an activating action on phospholipase DM derived from the Nocardiopsis strain, and $AlCl_3$, $CaCl_2$, $FeCl_3$, $FeSO_4$, $MgCl_2$, $SnCl_2$, sodium deoxycholate, ethanol, isopropanol, and t-butanol have an activating action on phospholipase DM drived from the Actinomadura strain. On the other hand, it is found that sodium dodecylsulfate and cetyl pyridinium chloride have an inhibiting action on phospholipase DM derived from the Nocardiopsis strain, acetyl pyridinium chloride has an inhibiting action on phospholipase DM derived from Actinomadura strain.

8. Method of measuring the activity of the enzyme (As stated hereinabove)

9. Method of Purification

About 15 liters of a culture medium (pH 6.0) composed of 3.0 g of soybean flour, 1.0% of corn steep liquor, 0.5 g of peptone, 0.1% of powdery yeast extract, 1.0 g of glucose, 0.25% of $NH_4NO_3$, 0.4% of $K_2HPO_4$, 0.01% of $MgSO_4.7H_2O$, and 0.1% of Tween-85 was put in a 30 liter jar fermentor, and sterilized at 120° C. for 15 minutes. Then, 1.5 liters of a seed culture was inoculated, and cultivated at 27° C. for 40 hours.

The seed culture had been prepared by putting 100 ml of an aqueous solution (pH 6.8) containing 1% of starch, 0.25% of $(NH_4)H_2PO_4$, 0.25% of peptone, 0.2% of $K_2HPO_3$ and 0.01% of $MgSO_4.7H_2O$ in a 500 ml Sakaguchi flask, sterilizing it with steam, inoculating one platinum loopful of spores of Nocardiopsis sp. No. 779 (PB 512) or Actinomadura sp. No. 362 (BP 511) into the culture medium, and cultivating it with shaking at 30° C. for 2 days at 120 rpm.

After the cultivation, solid materials of the cells were removed by centrifugation to obtain 13 liters of a supernatant liquid (0.54 u/ml in the case of using the Nocardiopsis strain; and 1.7 u/ml in the case of using the Actinomadura strain). The supernatant liquid was cooled to 5° C., and acetone kept at −20° C. was added. By centrifugation, precipitates containing phospholipase DM corresponding to fractions having an acetone concentration of 30 to 70% were collected. The precipitates were dissolved in Tris-maleic acid buffer (pH 6.0 in the case of using the Nocardiopsis strain, and pH 6.5 in the case of using the Actinomadura strain), dialyzed against the same buffer having a molarity of 0.02M, and passed through a DEAE-cellulose column equilibrated with the same buffer. Fractions which have passed through the column were collected. A palmitoyl gauze prepared by the method of Horiuti et al. [J. Biochem. 81, 1639 (1977)] was filled in a column. After washing the column fully with water, the collected fractions were charged onto the column to adsorp active components. The column was washed with 0.05M Tris-HCl buffer (pH 7.2) and then eluted with the same buffer containing 0.2% Triton X-100. Active fractions were collected and concentrated by using an ultrafiltration membrane (Type G-10T made by Bioengineering Co., Ltd.), then charged onto a column filled with Toyo-Pearl HW-55F (made by Toyo Soda Co., Ld.) as a gel fitration carrier, and passed through it by using distilled water. Active fractions were collected and lyophilized.

The dry powder was then dissolved in 0.025M imidazole-HCl (pH 7.4) (in the case of phospholipase DM derived from the Nocardiopsis strain), or 0.025M Tris-acetic acid (pH 8.3) (in the case of phospholipase DM derived from the Actinomadura strain). The solution was passed through a column filled with a polybuffer exchanger PBE$^{TN}$94 (20 ml) made by Pharmacia Fine Chemicals, Co. to adsorb active components. The column was then eluted by a pH gradient method using an eluting polybuffer made by the same company as above (pH 5.0). The eluted active fractions of phospholipase DM were collected and concentrated by an ultrafiltration membrane, and passed through a column filled with Sephadex G-75. Active fractions of phospholipase DM were collected and lyophilized.

As a result, phospholipase DM from the Nocardiopsis strain having a specific activity of 178.3 u/mg protein was recovered at an activity recovery ratio of about 40%. Furthermore, phospholipase DM from the Actinomadura strain having a specific activity of 218.3 u/mg protein was recovered at an activity recovery ratio of about 43%.

10. Isoelectric point

Phospholipase DM derived from the Nocardiopsis strain:

4.85±0.1 (measured by isoelectric focusing with Ampholine)

Phospholipase DM derived from the Actinomadura strain:

6.4±0.1 (measured by isoelectric focusing with Ampholine)

11. Transferring action

It is known that the conventional phospholipase D produces phosphatidic acid from lecithin and transfers it to a linear primary alcohol having 1 to 6 carbon atoms to form an ester, but does not form such an ester with a secondary alcohol. It has been found that the enzymes (phospholipases DM) used in accordance with this invention effect transfer to not only a broad range of primary alcohols including those which it has been described cannot be transferred by the known phospholipase D, but also secondary alcohols to form esters.

The phospholipase DM used in the process of this invention reacts in accordance with the method of experimenting the transferring action (the method of determining the formation of a transfer product by TLC) to be described hereinbelow, and catalyzes the reaction of forming a phospholipid-primary alcohol derivative between a $C_{10}$ primary alcohol such as geraniol and a phospholipid such as lecithin to form a primary alcohol derivative of the phospholipid. The known phospholipase D does not form the aforesaid derivative. Likewise, the phospholipase DM used in the process of this invention reacts in accordance with the method of determing the formation of a transfer product by TLC to be described hereinbelow, and catalyzes the reaction of forming a phospholipid-secondary alcohol derivative between a $C_4$ secondary alcohol such as 2-butanol and a phospholipid such as lecithin to form a secondary alcohol derivative of the phospholipid. The known phospholipase D does not form the aforesaid derivative.

According to the process of this invention, a primary or secondary alcohol derivative of a phospholipid represented by the following formula (I)

wherein A and R are as defined hereinabove, can be produced by reacting the phospholipid of formula (II) with the primary or secondary alcohol of (1) to (4) in the presence of the phospholipase DM described above in detail. The phospholipase DM needs not to be a pure product, and a crude product may also be used. It may also be used after it has been immobilized to a suitable support, for example particles or films of various resins or inorganic materials such as a polypropylene film, Celite particles and glass beads.

The reaction can be carried out by contacting the phospholipid of formula (II) with the primary or secondary alcohol selected from (1) to (4) in the presence of phospholipase DM, preferably in the presence of a solvent. The solvent may be an aqueous solvent or a mixture of an aqueous solvent and an organic solvent. The primary or secondary alcohol itself may also serve concurrently as a solvent. Solvents containing additives which do not inhibit the enzymatic catalytic action of the phospholipase DM may also be used. For example, the solvent may contain suitable additives which serve to promote the aforesaid action or stabilize the enzyme. For example, the solvent may be an aqueous solvent containing a buffer such as acetic acid, citric acid or phosphoric acid or a neutral salt such as calcium chloride. Examples of the organic solvent are the aforesaid primary or secondary alcohols; aliphatic hydrocarbons such as n-heptane and n-hexane; alicyclic hydrocarbons such as cyclopentane, cyclohexane and cyclobutane; aromatic hydrocarbons such as benzene, toluene and xylene; ketones such as acetone and methyl isopropyl ketone; ethers such as dimethyl ether, diethyl ether and diisopropyl ether; esters such as methyl acetate and ethyl acetate; halogenated hydrocarbons such as carbon tetrachloride, chloroform and methylene chloride; amides such as dimethylformamide; and sulfoxides such as dimethyl sulfoxide.

When a mixture of the aqueous solvent and the organic solvent is used, the mixing ratio of the two can be suitably selected. For example, the ratio (V/V) of the aqueous solvent to the organic solvent may range from 50:1 to 1:10.

The mole ratio of the reactants, the amount of the phospholipase DM, and the amount of the solvent can be properly selected. For example, the primary or secondary alcohol may be used in an amount of about 1 to about 1000 moles, preferably about 10 to about 1000 moles, per mole of the phospholipid of formula (II). The amount of the phospholipase DM may, for example, be about 10 to about 100,000 units, preferably about 100 to about 1000 units per gram of the phospholipid of formula (II). The amount of the solvent may, for example, be about 10 to about 500 times the volume of the phospholipid of formula (II).

The reaction proceeds at room temperature, and no cooling or heating is particularly required. If desired, the reaction may be carried out under cooling or heating, for example at a reaction temperature of about 0° C. to about 90° C., preferably about 20° to about 60° C. The reaction time can also be properly selected, and may, for example, be about 1 minute to about 10 days, preferably about 0.1 to about 72 hours, more preferably about 1 to about 72 hours. As required, the reaction time may properly be changed by monitoring the proceeding of the reaction in accordance with, for example, thin-layer chromatography (TLC), and confirming the formation of the desired product.

Contacting of the phospholipid of formula (II) with the primary or secondary alcohol in the presence of phospholipase DM can be carried out in any desired mode, but usually under stirring or shaking conditions. When the enzyme is used in the form of an immobilized enzyme on a suitable particulate or film-like support as exemplified above, the reaction mixture may be passed through the immobilized enzyme film or the immobilized enzyme particle layer by means of a circulating pump.

The phospholipid-primary or secondary alcohol derivative of formula (I) formed by the above reaction may be used either directly or after it has been precipitated in the form of a salt. Or it may be isolated and purified by suitable known methods such as silica column chromatography, alumina column chromatography, high performance liquid chromatography, countercurrent distribution, gel filtration and adsorption chromatography.

According to the process of this invention, the phospholipid-primary or secondary alcohol derivative of formula (I) can be produced by reacting the phospholipid of formula (II) with the primary or secondary alcohol selected from the groups (1) to (4) in the presence of the phospholipase DM in the manner described hereinabove.

The resulting phospholipid-primary or secondary alcohol derivatives of formula (I) obtained have excellent surface-activating action and exert great effects on the permeability of cell membranes. Accordingly, the derivatives of formula (I) are useful as a liposome-forming substrate, or as an emulsifier for cosmetics such as cream and lotion, fat solutions for transfusion, and agricultural chemicals such as pesticides and herbicides.

Furthermore, in many cases, phospholipids are known to have unique physiological properties. Since many of the derivatives of formula (I) obtained by the process of this invention have a similar structure to the phospholipids, they are expected to exhibit various biological activities. Furthermore, by transferring to a phospholipid a pharmacologically active compound containing a primary or secondary alcoholic hydroxyl group or having a primary or secondary alcoholic hydroxyl group introduced thereinto, it is possible to weaken the pharmacological side-effects of the compound, or to increase its pharmacological efficacy and reduce its dosage. Moreover, the pharmacologically active compound may be transferred to a phospholipid and used as a carrier for concentrating the compound accurately on a particular lesion. Furthermore, it also serves as a useful protective group for a pharmacologically active compound.

The derivatives of formula (I) in accordance with this invention are also useful as intermediates for synthesis of chemicals including various medicines. For example, derivatives obtained by transferring an alcohol having halogen or amino which has high reactivity may be utilized for this purpose. A labelled phospholipid derivative may be obtained by transferring a primary or secondary alcohol labelled with tritium or $^{14}C$, and utilized for elucidating the metabolic pathways of phospholipids.

The following examples illustrate the process of this invention in greater detail.

REFERENTIAL EXAMPLE 1

Preparation of phospholipases

In accordance with the Method of Purification in section (9) above, phospholipases DM were obtained in the activity recovery ratios and specific activities described in the aforesaid section using Nocardiopsis sp. No. 779 (FERM-P No. 6133; BP 512) and Actinomadura sp. No. 362 (FERM-P No. 6132: BP 511).

EXAMPLE 1

Runs Nos. 1 to 85)

The following phospholipids of formula (II) were respectively reacted with the various primary alcohols shown in Table 2 below in the presence of the phospholipases DM in accordance with the method of determining the formation of transfer products (phospholipids-primary alcohols) by TLC. The Rf values of the products are given in Table 2.

Substrate I: L-alpha-lecithin, beta, gamma-dimyristoyl (Sigma Co.) (1,2-ditetradecanoyl-Sn-glycerol-3-phosphorylcholine)

Substrate II: L-alpha-lecithin, beta, gamma-dihexadecyl (Calbiochem-Behring Co.) (1,2-dihexa-decyl-Sn-glycerol-3-phosphorylcholine)

Substrate III: (L-alpha-lecithin, beta, gamma-hexadecylidine (ditto) (1,2-cyclohexadecylidene-Sn-gycerol-3-phosphorylcholine)

Substrate IV: beta-Lecithin-alpha,gamma-dipalmitoyl (ditto) (1,3-dihexadecanoyl-glycerol-2-phosphorylcholine)

Method of determining the formation of the transfer product by TLC:

0.1 ml (0.2–1.0 u/0.1 ml) of an aqueous solution of the phospholipase DM was added to a reaction solution having the following formulation.

| | |
|---|---|
| 1% phospholipid emulsion | 0.1 ml |
| 0.4 M acetate buffer (pH 5.7) | 0.1 ml |
| 0.1 M aqueous calcium chloride solution | 0.05 ml |
| Distilled water | 0.1 ml |
| 10% solution of the primary or secondary alcohol | 0.1 ml |

The mixture was left to stand at 37° C. for 1 to 5 hours.

The 1% phospholipid emulsion was prepared by adding 1 ml of diethyl ether and 10 ml of distilled water to 100 mg of the phospholipid, and subjecting the mixture to ultrasonication for 5 minutes with ice cooling at 600W and 20 KHz. The 10% primary or secondary alcohol solution was prepared by adding water or an organic solvent such as diethyl ether and acetone as required.

After standing, 0.2 ml of a 50 mM aqueous solution of EDTA(ethylenediamine tetraacetic acid) was added, and 5 ml of a mixture of chloroform and methanol (2:1 by volume) was added. The mixture was vigorously stirred to extract the lipid (product). The resulting suspension was centrifuged for 10 minutes at 2000 x g. The lower chloroform layer was separated, dried under reduced pressure at 30° C., and dissolved in 75 microliters of a mixture of chloroform and methanol (1:1 by volume) to form a sample for TLC. Ten microliters of the sample was spotted on a thin layer of silica gel (Funagel 60 Å, 20 cm×20 cm, a product of Funakoshi Yakuhin K. K.), and the silica gel layer was developed with a mixture of diisobutyl ketone, acetic acid and water (40:25:5). The following reagents were used for detecting the spots. When a spot of a phospholipid other than those of the undecomposed substrate and its hydrolysis product (phosphatidic acid and its analogs) was detected, it was determined to be the transfer product.

Detecting reagents

Color-formation of phosphoric acid: Zinzade's reagent (Beiss. U. J. Chromatog., 13, 104, 1964)

Color formation of primary amine: Ninhydrin reagent (a 0.25% acetone solution of ninhydrin)

Color formation of secondary amine: Hypochloritebenzidine reagent (M. C. Bischel et al., Biochim. Biophys. Acta, 70, 598, 1963)

Color formation of purine and pyrimidine: Fluoresceinammonia reagent (T. Wieland, et al., Angew. Chem., 63, 511, 1951)

Color formation of a glycol linkage: Periodic acid-Schiff reagent (N. Shaw, Biochim. Biophys. Acta, 164, 435, 1968)

Color formation of 17-ketosteroid: m-dinitrobenzene reagent (B. P. Lisboa, J. Chromatog., 16, 136, 1964)

COMPARATIVE EXAMPLE 1

The procedure of Example 1 was repeated except that known phospholipase D derived from cabbage (P-L Biochemicals, Inc.) was used instead of the phospholipase DM in Example 1. It was found that with this known phospholipase, no transfer products were obtained with the primary alcohols indicated in Table 2 below.

TABLE 2

| Run No. | Primary alcohol added | Rf value of the transfer product | | | |
|---|---|---|---|---|---|
| | | Substrate I | Substrate II | Substrate III | Substrate IV |
| | Not added | | | | |
| | Phosphatidic acid | 0.59 | 0.49 | 0.44 | 0.58 |
| | Substrate | 0.27 | 0.25 | 0.20 | 0.30 |
| 1 | 1-Heptanol | 0.74 | 0.60 | 0.50 | 0.70 |
| 2 | 1-Octanol | 0.74 | 0.58 | 0.50 | 0.72 |
| 3 | 3-Ethyl-1-hexanol | 0.70 | 0.60 | 0.50 | 0.72 |
| 4 | 1-Nonanol | 0.75 | 0.60 | 0.52 | 0.72 |
| 5 | 1-Decanol | 0.78 | 0.62 | 0.54 | 0.70 |
| 6 | 1-Undecanol | 0.75 | 0.62 | 0.52 | 0.73 |
| 7 | 1-Dodecanol | 0.78 | 0.63 | 0.54 | 0.76 |
| 8 | 1-Tetradecanol | 0.76 | 0.62 | 0.55 | 0.78 |
| 9 | 1-Hexadecanol | 0.76 | 0.64 | 0.55 | 0.75 |
| 10 | 1-Octadecanol | 0.80 | 0.64 | 0.55 | 0.76 |
| 11 | 1-Eicosanol | 0.80 | 0.68 | 0.57 | 0.76 |
| 12 | 1-Docosanol | 0.78 | 0.66 | 0.56 | 0.80 |
| 13 | 1-Hexacosanol | 0.78 | 0.68 | 0.57 | 0.78 |
| 14 | Geraniol | 0.73 | 0.61 | 0.55 | 0.72 |
| 15 | Citronellol | 0.70 | 0.66 | 0.55 | 0.72 |
| 16 | Farnesol | 0.70 | 0.65 | 0.57 | 0.74 |
| 17 | Phytol | 0.75 | 0.68 | 0.57 | 0.74 |
| 18 | 1,6-Hexanediol | 0.63 | 0.56 | 0.45 | 0.62 |
| 19 | 1,2,6-hexanetriol | 0.52 | 0.47 | 0.40 | 0.54 |
| 20 | Sorbitol | 0.47 | 0.42 | 0.32 | 0.44 |
| 21 | Mannitol | 0.47 | 0.42 | 0.30 | 0.48 |
| 22 | 2-n-Butyl-2-ethyl-1,3-propanediol | 0.62 | 0.52 | 0.46 | 0.67 |
| 23 | 2-Ethyl-1,3-hexanediol | 0.68 | 0.58 | 0.49 | 0.69 |
| 24 | 1,1,1-tris(hydroxymethyl)propane | 0.45 | 0.40 | 0.35 | 0.47 |
| 25 | 3,3-bis(Hydroxymethyl) heptane | 0.68 | 0.59 | 0.50 | 0.70 |
| 26 | 1,10-decanediol | 0.69 | 0.58 | 0.54 | 0.70 |
| 27 | 1,12-Dodecanediol | 0.70 | 0.58 | 0.56 | 0.70 |
| 28 | 6-Amino-1-hexanol | 0.44 | 0.35 | 0.28 | 0.48 |
| 29 | Triethanolamine | 0.47 | 0.40 | 0.36 | 0.49 |
| 30 | N—butyldiethanolamine | 0.49 | 0.45 | 0.38 | 0.53 |
| 31 | Sphingosine | 0.64 | 0.58 | 0.52 | 0.63 |
| 32 | Pantothenyl alcohol | 0.39 | 0.39 | 0.41 | 0.52 |
| 33 | Serine ethyl ester | 0.41 | 0.43 | 0.38 | 0.48 |
| 34 | Dihydroxyethylglysine | 0.48 | 0.45 | 0.38 | 0.56 |
| 35 | 16-Hydroxyhexadecanoic acid | 0.66 | 0.55 | 0.48 | 0.68 |
| 36 | Monolaurin | 0.67 | 0.58 | 0.53 | 0.68 |
| 37 | Monoolein | 0.70 | 0.60 | 0.55 | 0.68 |
| 38 | 2-Hydroxyethyl methacrylate | 0.56 | 0.47 | 0.43 | 0.55 |
| 39 | Triethylene glycol | 0.50 | 0.44 | 0.40 | 0.52 |
| 40 | Diethylene glycol monobutyl ether | 0.68 | 0.57 | 0.52 | 0.67 |
| 41 | Benzyl alcohol | 0.70 | 0.60 | 0.55 | 0.66 |
| 42 | β-Phenethyl alcohol | 0.65 | 0.53 | 0.53 | 0.62 |
| 43 | 3-Phenyl-1-propanol | 0.68 | 0.59 | 0.57 | 0.67 |
| 44 | Cinnamyl alcohol | 0.68 | 0.56 | 0.57 | 0.68 |
| 45 | p-Chlorobenzyl alcohol | 0.70 | 0.62 | 0.55 | 0.66 |
| 46 | p-Aminophenethyl alcohol | 0.62 | 0.54 | 0.49 | 0.62 |
| 47 | N—ethyl-N—(2-hydroxyethyl)-m-toluidine | 0.62 | 0.57 | 0.50 | 0.62 |
| 48 | β-Hydroxyethylaniline | 0.62 | 0.56 | 0.47 | 0.60 |
| 49 | N—(2-cyanoethyl)-N—2-hydroxyethylaniline | 0.63 | 0.56 | 0.47 | 0.64 |
| 50 | N—phenyldiethanolamine | 0.52 | 0.40 | 0.40 | 0.48 |
| 51 | Anisic alcohol | 0.70 | 0.66 | 0.54 | 0.68 |
| 52 | 1,4-Di(2-hydroxyethoxy) benzene | 0.65 | 0.60 | 0.52 | 0.63 |
| 53 | Ethylene glycol monophenyl ether | 0.69 | 0.60 | 0.50 | 0.67 |
| 54 | Mephenesine | 0.62 | 0.51 | 0.47 | 0.64 |
| 55 | 2-Hydroxyethylsalicylic acid | 0.63 | 0.57 | 0.52 | 0.65 |
| 56 | 1,4-Dihydromethyl-cyclohexane | 0.66 | 0.62 | 0.58 | 0.65 |
| 57 | Retinol (vitamin A alcohol) | 0.74 | 0.66 | 0.60 | 0.72 |
| 58 | O,O—bis(2-hydroxyethyl) tetrabromobisphenol | 0.67 | 0.63 | 0.58 | 0.67 |
| 59 | 2-Naphthalene ethanol | 0.70 | 0.65 | 0.59 | 0.68 |
| 60 | Corticosterone | 0.64 | 0.58 | 0.48 | 0.65 |
| 61 | Cortisone | 0.66 | 0.58 | 0.48 | 0.65 |
| 62 | Prednisolone | 0.66 | 0.60 | 0.50 | 0.65 |
| 63 | Prednisone | 0.65 | 0.58 | 0.48 | 0.65 |
| 64 | Galactono-gamma-lactone | 0.42 | 0.39 | 0.31 | 0.39 |
| 65 | N—(2-hydroxyethyl)-phthalimide | 0.61 | 0.50 | 0.46 | 0.60 |
| 66 | 2-(3-indole)ethanol | 0.72 | 0.61 | 0.51 | 0.66 |
| 67 | 2-(2-Hydroxyethyl)-pyridine | 0.48 | 0.41 | 0.37 | 0.50 |

TABLE 2-continued

| Run No. | Primary alcohol added | Rf value of the transfer product | | | |
|---|---|---|---|---|---|
| | | Substrate I | Substrate II | Substrate III | Substrate IV |
| 68 | Pyridoxine | 0.42 | 0.38 | 0.33 | 0.41 |
| 69 | N—(2-hydroxyethyl)-morpholine | 0.40 | 0.40 | 0.37 | 0.42 |
| 70 | 5-Hydroxymethyl-cytosine | 0.36 | 0.30 | 0.30 | 0.37 |
| 71 | Cytidine | 0.48 | 0.38 | 0.29 | 0.41 |
| 72 | Uridine | 0.50 | 0.36 | 0.32 | 0.40 |
| 73 | Arabinocytidine | 0.46 | 0.35 | 0.27 | 0.43 |
| 74 | Thiamine | 0.19 | 0.20 | 0.11 | 0.21 |
| 75 | 2-(2-Hydroxyethyl)-piperazine | 0.52 | 0.39 | 0.35 | 0.52 |
| 76 | Adenosine | 0.52 | 0.33 | 0.30 | 0.46 |
| 77 | Guanosine | 0.49 | 0.35 | 0.30 | 0.43 |
| 78 | Cyclocytidine | 0.48 | 0.37 | 0.28 | 0.43 |
| 79 | N,N—Dibutyl ethanolamine | 0.61 | 0.55 | 0.45 | 0.60 |
| 80 | N—(3-Aminopropyl)-diethanolamine | 0.36 | 0.30 | 0.30 | 0.36 |
| 81 | Trimethylol propane | 0.58 | 0.48 | 0.42 | 0.58 |
| 82 | Dipentaerthritol | 0.42 | 0.39 | 0.34 | 0.42 |
| 83 | Gluconic acid | 0.34 | 0.30 | 0.30 | 0.34 |
| 84 | 6-Chloro hexanol | 0.63 | 0.57 | 0.48 | 0.62 |
| 85 | N—Stearoyl ethanolamine | 0.48 | 0.43 | 0.37 | 0.50 |

The samples were subjected to a color reaction with the Zinzade's reagent. Those having special functional groups were subjected to a color reaction by using the other reagents mentioned hereinabove.

EXAMPLE 2

(Runs Nos. 1 to 28)

Four hundred milligrams of L-alpha-lecithin, beta,-gamma-dimyristoyl (a product of Sigma Chemical Company; purity 98%), 1 ml of diethyl ether and 10 ml of distilled water were put in an ultrasonication cell, and with ice cooling ultrasonicated for 5 minutes at 600 W and 20 KHz to give an milk-white emulsion.

Two milliliters of the lecithin emulsion (80 mg of lecithin), 2 ml of a 0.4M acetate buffer (pH 5.7), 1 ml of a 0.1M aqueous solution of calcium chloride and 2 ml of a 10% diethyl ether solution of beta-hydroxyethylaniline were put in a test tube with a ground stopper. Then, 2 ml of an aqueous solution of phospholipase DM (2.5 u/ml) was added and well mixed. The mixture was left to stand at 37° C. for 3 hours. To the reaction mixture was added 0.5 ml of 0.5N hydrochloric acid, and 15 ml of a mixture of chloroform and methanol (2:1) was further added. They were vigorously mixed to extract the phospholipid. The mixture was centrifuged for 10 minutes at 2,000 x g, and the lower chloroform layer was separated.

Chloroform (10 ml) was again added to the upper aqueous layer and the same extracting operation was carried out. The extracts were combined and then washed with 10 ml of 0.02N hydrochloric acid. By centrifugation, the chloroform layer was again separated from this mixture, dried under reduced pressure, and dissolved in 1 ml of a mixture of n-hexane, 2-propanol and water (60:80:7).

Twenty microliters of this sample was spotted on a thin layer of silica gel (Funagel, a product of Funakoshi Yakuhin K. K.), and the silica gel layer was developed with a solvent system composed of diisobutyl ketone, acetic acid and water (40:25:5). Three phospholipids were detected, and two of them agreed in Rf values with phosphatidic acid an lecithin.

This sample was purified by high-performance liquid chromatography. The column used was a Radial-Pak cartridge silica, 8 mm × 10 cm, (made by Waters Co., and the eluent used was a mixture of n-hexane, 2-propanol and water (60:80:7). The flow rate was 2 ml/min. For detecting peaks, a 441-type ultraviolet detector (made by Waters Co.) for determining an absorption at 214 nm and a R401-type differential refractometer (made by Waters Co.) were used. The sample was injected into the column four times in an amount of 0.25 ml each time.

Three components included in the sample, i.e. beta-hydroxyethylaniline, phosphatidic acid, and betahydroxyethylaniline ester of phosphatidic acid, were separated. Then, the undecomposed lecithin adsorbed on the column was eluted with n-hexane-2-propanol-water (60:80:14) as an eluent. The three phospholipids obtained were again purified by high-performance liquid chromatography by the same procedure.

The proportions of the three phospholipids were as follows:

Phosphatidic acid: about 10 mole %
Transfer product: about 80 mole %
Undecomposed lecithin: about 10 mole %

As a result, about 40 mg of a beta-hydroxyethylaniline ester of phosphatidic acid as a purified transfer product was obtained. The IR spectrum of this compound was measured by a liquid film method using an infrared specrophotometer (Model A202, a product of Nippon Bunko K. K.) The results are shown in Table 3 (Run No. 14).

The above procedure was repeated using the other primary alcohols shown in Table 3. The results are shown in Table 3 (Runs Nos. 1 to 13 and 15 to 28). The primary alcohol was added in the above procedure as a solution in water, diethyl ether or acetone selected as required depending upon the solubility of the alcohol.

TABLE 3

IR spectra of transfer products of 1,2-ditetradecanoyl-sn-glycerol-3-phosphoric acid with various alcohols

| Run No. | Alcohol as an acceptor in a transfer reaction | IR $\nu_{max}$ |
|---|---|---|
| 1 | 1-Heptanol | 2920, 2850, 1740, 1460, 1375, 1240, 1170, 1105, 1075, 830, 720 |
| 2 | 1-Hexadecanol | 2920, 2850, 1735, 1465, 1380, 1230, 1165, 1105, 1075, 840, 720 |
| 3 | 1-Docosanol | 2920, 2850, 1740, 1740, 1380, 1230, 1170, 1105, 1075, 840, 720 |
| 4 | Geraniol | 2920, 2850, 1740, 1665, 1455, 1380, 1215, 1090, 1075, 1000, 830 |
| 5 | Phytol | 3370, 2920, 2850, 1735, 1460, 1380, 1220, 1100, 1060, 1010, 830, 720 |
| 6 | 1,6-Hexanediol | 3380, 2930, 2850, 1735, 1470, 1380, 1230, 1105, 1070, 850, 720 |
| 7 | 1,12-Dodecanediol | 3380, 2920, 2850, 2740, 1465, 1380, 1230, 1170, 1100, 1070, 980, 850 |
| 8 | 2-n-Butyl-2-ethyl-1,3-propanediol | 3380, 2920, 2850, 1735, 1465, 1380, 1230, 1170, 1070, 980, 840, 760, 720 |
| 9 | Pantothenyl alcohol | 3380, 2940, 2860, 1740, 1650, 1550, 1470, 1380, 1230, 1175, 1110, 1075, 860, 805, 720 |
| 10 | Diethylene glycol | 2920, 2850, 1740, 1465, 1380, |

TABLE 3-continued

IR spectra of transfer products of 1,2-ditetradecanoyl-sn-glycerol-3-phosphoric acid with various alcohols

| Run No. | Alcohol as an acceptor in a transfer reaction | IR $\nu_{max}$ |
|---|---|---|
|  | monobutyl ether | 1245, 1145, 1110, 1050, 1000, 860, 760, 720 |
| 11 | Monolaurin | 3400, 2930, 2860, 1740, 1470, 1380, 1235, 1210, 1180, 1110, 1050, 1000, 860, 720 |
| 12 | Benzyl alcohol | 3380, 2920, 2850, 1740, 1500, 1470, 1410, 1380, 1250, 1170, 1100, 1075, 860, 730, 695, 595 |
| 13 | p-Chlorobenzyl alcohol | 3320, 2920, 2850, 1740, 1495, 1470, 1410, 1380, 1230, 1175, 1100, 1040, 1010, 880, 805, 720, 660 |
| 14 | β-Hydroxyethylaniline | 3380, 2920, 2850, 1740, 1605, 1500, 1470, 1380, 1230, 1180, 1065, 990, 830, 750, 720, 695 |
| 15 | 2-Hydroxyethyl-salicylic acid | 3220, 2940, 2860, 1740, 1680, 1615, 1590, 1490, 1470, 1380, 1300, 1250, 1215, 1160, 1060, 975, 860, 760, 720, 700 |
| 16 | 1,4-Dihydroxy-methylcyclohexane | 3350, 2920, 2850, 1740, 1465, 1380, 1230, 1170, 1110, 1030, 870, 720 |
| 17 | 2-Naphthaleneethanol | 2920, 2850, 1740, 1465, 1380, 1240, 1160, 1000, 1060, 1020, 850, 820, 740 |
| 18 | Cortisone | 3400, 2920, 2850, 1735, 1700, 1670, 1460, 1380, 1230, 1170, 1100, 1050, 995, 860, 745 |
| 19 | O,O—bis(2-hydroxyethyl) tetrabromophenol | 3420, 2920, 2850, 1735, 1590, 1535, 1465, 1385, 1260, 1170, 1060, 970, 905, 870, 740 |
| 20 | 2-(3-Indole)ethanol | 3400, 2940, 2860, 1730, 1675, 1600, 1580, 1460, 1380, 1270, 1125, 1075, 860, 740, 700 |
| 21 | Pyridoxine | 3300, 2920, 2850, 1730, 1540, 1465, 1380, 1220, 1060, 1030, 855 |
| 22 | 5-Hydroxy-methylcytosine | 2920, 2850, 1735, 1675, 1550, 1470, 1380, 1200, 1175, 1065, 1020, 860, 720 |
| 23 | Thiamine | 3350, 3200, 2920, 2850, 1735, 1660, 1600, 1560, 1465, 1450, 1380, 1230, 1170, 1090, 1060, 980, 910, 815, 750, 720 |
| 24 | Adenosine | 3350, 3200, 2920, 2850, 1735, 1465, 1410, 1380, 1230, 1200, 1170, 1080, 810, 720 |
| 25 | N,N—Dibutyl ethanolamine | 3400, 2950, 2860, 1740, 1640, 1460, 1380, 1240, 1170, 1060, 980, 920, 820, 720 |
| 26 | Gluconic acid | 3400, 2930, 2850, 1720, 1630, 1460, 1375, 1235, 1095, 1060, 980, 940, 860, 720 |
| 27 | 6-Chloro hexanol | 2930, 2850, 1740, 1480, 1375, 1240, 1160, 1060, 880, 720 |
| 28 | N—Stearoyl ethanolamine | 3350, 2940, 2850, 1740, 1650, 1540, 1450, 1240, 1100, 1060, 720 |

EXAMPLE 3

(Runs Nos. 1 to 24)

A mixture of 400 mg of L-alpha-lecithin beta, gamma-dihexadecyl (Calbiochem-Behring Co.), 1 ml of diethyl ether and 10 ml of distilled water was emulsified in the same way as in Example 2. By the same method as in Example 2, 2 ml of the emulsion was reacted with a 10% aqueous solution of thiamine hydrochloride as a primary alcohol. The reaction mixture was treated in the same way as in Example 2 to give 30 mg of a transfer product. The IR spectrum of this product is shown in Table 4 (Run No. 23).

The above procedure was repeated using the other primary alcohols indicated in Table 4. The results are shown in Table 4 (Runs Nos. 1 to 22 and 24).

TABLE 4

IR spectra of transfer products of 1,2-dihexadecyl-sn-glycerol-3-phosphoric acid with various alcohols

| Run No. | Alcohol as an acceptor in a transfer reaction | IR $\nu_{max}$ |
|---|---|---|
| 1 | 1-Heptanol | 2920, 2850, 1465, 1380, 1230, 1110, 1015, 885, 720 |
| 2 | 1-Hexadecanol | 2920, 2850, 1465, 1380, 1230, 1120, 1050, 1010, 885, 720 |
| 3 | 1-Docosanol | 2920, 2850, 1470, 1380, 1230, 1115, 1010, 890, 720 |
| 4 | Geraniol | 2920, 2850, 1465, 1380, 1230, 1115, 1015, 885, 720 |
| 5 | Phytol | 3400, 2920, 2855, 1470, 1380, 1230, 1110, 1040, 1015, 890, 720 |
| 6 | 1,6-Hexanediol | 3380, 2920, 2850, 1465, 1380, 1230, 1100, 1040, 1020, 865, 720 |
| 7 | 1,12-Dodecanediol | 3380, 2920, 2850, 1465, 1380, 1230, 1100, 1020, 970, 870, 720 |
| 8 | 2-n-butyl-2-ethyl-1,3-propanediol | 3380, 2920, 2860, 1470, 1380, 1235, 1105, 1040, 875, 720 |
| 9 | Pantothenyl alcohol | 3350, 2930, 2860, 1650, 1540, 1470, 1380, 1220, 1100, 1060, 990, 860, 755, 720 |
| 10 | Diethylene glycol monobutyl ether | 2920, 2850, 1470, 1380, 1225, 1100, 1050, 990, 860, 770, 720 |
| 11 | Monolaurin | 3400, 2930, 2860, 1720, 1465, 1380, 1235, 1100, 1050, 1000, 865, 720 |
| 12 | Benzyl alcohol | 3420, 2930, 2860, 1465, 1380, 1235, 1100, 1040, 1020, 865, 720, 695 |
| 13 | p-Chlorobenzyl alcohol | 3380, 2920, 2850, 1470, 1380, 1230, 1100, 1040, 1010, 870, 810, 720, 660 |
| 14 | β-Hydroxyethylaniline | 3380, 2920, 2850, 1605, 1500, 1465, 1380, 1230, 1095, 1060, 990, 840, 755, 720, 695 |
| 15 | 2-Hydroxyethylsalicylic acid | 3250, 2940, 2860, 1675, 1610, 1585, 1470, 1420, 1380, 1320, 1300, 1250, 1220, 1155, 1105, 1060, 980, 860, 800, 755, 720, 700, 530 |
| 16 | 1,4-Dihydroxy-methylcyclohexane | 3380, 2920, 2850, 1465, 1380, 1230, 1150, 1100, 1070, 840, 720 |
| 17 | 2-Naphthalene ethanol | 2920, 2850, 1465, 1380, 1235, 1100, 1060, 1020, 895, 850, 820, 740 |
| 18 | Cortisone | 3400, 2920, 2850, 1700, 1660, 1465, 1380, 1230, 1100, 1055, 860, 740 |
| 19 | O,O-bis(2-hydroxyethyl) tetrabromobisphenol | 3400, 2920, 2850, 1590, 1535, 1465, 1380, 1240, 1095, 1040, 975, 905, 870, 740 |
| 20 | 2-(3-indole) ethanol | 3400, 2930, 2850, 1670, 1600, 1580, 1465, 1380, 1240, 1115, 1070, 860, 740, 700 |
| 21 | Pyridoxine | 3300, 2920, 2850, 1545, 1465, 1380, 1230, 1100, 1060, 1010, 860 |
| 22 | 5-Hydroxymethylcytosine | 2920, 2850, 1675, 1540, 1465, 1380, 1220, 1145, 1090, 1050, 860, 720 |
| 23 | Thiamine | 3340, 3160, 2920, 2850, 1645, 1595, 1555, 1465, 1440, 1375, 1230, 1090, 1055, 910, 815, 750, 720 |
| 24 | Adenosine | 3350, 3200, 2920, 2850, 1695, 1465, 1415, 1380, 1230, 1100, |

TABLE 4-continued

IR spectra of transfer products of 1,2-dihexadecyl-sn-glycerol-3-phosphoric acid with various alcohols

| Run No. | Alcohol as an acceptor in a transfer reaction | IR $\nu_{max}$ |
|---|---|---|
| | | 1060, 810, 720 |

EXAMPLE 4

(Runs Nos. 1 to 24)

Four hundred milligrams of L-alpha-lecithin beta, gamma-hexadecylidine (a product of Calbiochem-Behring Co. was emulsified in the same way as in Example 2. The emulsified in an amount corresponding to 80 mg of the phosholipid was used, and geraniol was added as an acceptor in a transfer reaction. The same reaction, extraction and purification were carried out as in Example 2 to give 50 mg of the transfer product. The IR spectrum of this product is shown in Table 5 (Run No. 4).

The above procedure was repeated using the other primary alcohols indicated in Table 5. The results are shown in Table 5 (Runs Nos. 1 to 3 and 5 to 24).

TABLE 5

IR spectra of transfer products of 1,2-cyclohecadecylidene-sn-glycerol-3-phosphoric acid with various alcohols

| Run No. | Alcohol as an acceptor in a transfer reaction | IR $\nu_{max}$ |
|---|---|---|
| 1 | 1-Heptanol | 2920, 2850, 1465, 1380, 1225, 1090, 1020, 885, 720 |
| 2 | 1-Hexadecanol | 2920, 2850, 1465, 1380, 1230, 1100, 1010, 880, 720 |
| 3 | 1-Docosanol | 2920, 2850, 1465, 1380, 1225, 1090, 1020, 870, 720 |
| 4 | Geraniol | 2920, 2850, 1465, 1380, 1220, 1120, 1000, 885, 720 |
| 5 | Phytol | 2920, 2850, 1465, 1380, 1220, 1100, 1025, 860, 720 |
| 6 | 1,6-Hexanediol | 3380, 2920, 2850, 1465, 1380, 1220, 1120, 1040, 850, 720 |
| 7 | 1,12-Dodecanediol | 3380, 2920, 2850, 1465, 1380, 1225, 1120, 1030, 850, 720 |
| 8 | 2-n-Butyl-2-ethyl-1,3-propanediol | 3380, 2920, 2850, 1465, 1380, 1230, 1100, 1050, 975, 840, 765, 720 |
| 9 | Pantothenyl alcohol | 3350, 2920, 2850, 1650, 1535, 1465, 1380, 1220, 1140, 1040, 870, 755, 720 |
| 10 | Diethylene glycol monobutyl ether | 2920, 2850, 1465, 1380, 1230, 1100, 1050, 990, 870, 760, 720 |
| 11 | Monolaurin | 3380, 2920, 2850, 1720, 1465, 1380, 1220, 1190, 1105, 1050, 995, 860, 720 |
| 12 | Benzyl alcohol | 3380, 2920, 2850, 1500, 1465, 1220, 1130, 1060, 870, 720, 695 |
| 13 | p-Chlorobenzyl alcohol | 3340, 2920, 2850, 1500, 1470, 1380, 1225, 1135, 1065, 1010, 870, 800, 720, 660 |
| 14 | β-Hydroxyethylaniline | 3400, 2920, 2850, 1605, 1500, 1470, 1385, 1220, 1130, 1060, 1000, 870, 840, 750, 720, 695 |
| 15 | 2-Hydroxyethyl-salicylic acid | 3250, 2920, 2850, 1675, 1610, 1585, 1465, 1420, 1380, 1300, 1220, 1155, 1100, 1055, 990, 860, 800, 755, 720, 700 |
| 16 | 1,4-Dihydroxymethyl-cyclohexane | 3350, 2920, 2850, 1465, 1380, 1230, 1130, 1100, 1065, 855, 720 |
| 17 | 2-Naphthaleneethanol | 2920, 2850, 1465, 1380, 1230, 1100, 1055, 1010, 895, 855, 820, 740 |
| 18 | Cortisone | 3400, 2920, 2850, 1700, 1660, 1465, 1380, 1220, 1105, 1070, 990, 870, 740 |
| 19 | 0,0-bis(2-hydroxyethyl) tetrabromobisphenol | 3400, 2920, 2850, 1595, 1535, 1470, 1380, 1230, 1100, 1050, 980, 905, 870, 740 |
| 20 | 2-(3-Indole)ethanol | 3400, 2920, 2850, 1675, 1600, 1580, 1465, 1380, 1230, 1105, 1060, 860, 740, 700 |
| 21 | Pyridoxine | 3400, 2920, 2850, 1540, 1465, 1380, 1220, 1085, 1020, 965, 940, 850, 750 |
| 22 | 5-Hydroxymethylcytosine | 2920, 2850, 1675, 1540, 1465, 1380, 1220, 1140, 1080, 1030, 850, 720 |
| 23 | Thiamine | 3340, 3200, 2920, 2850, 1645, 1590, 1560, 1465, 1440, 1380, 1220, 1095, 1040, 910, 815, 760, 720 |
| 24 | Adenosine | 3340, 3200, 2920, 2850, 1465, 1410, 1380, 1215, 1090, 1050, 2-Hydroxyethylsalicylic 720 |

EXAMPLE 5

(Runs Nos. 1 to 24)

Four hundred milligrams of beta-lecithin, alpha, gamma-dihexadecanoyl (a product of Calbiochem-Behring Co.) was emulsified in the same way as in Example 2. The emulsion was used in an amount corresponding to 80 mg of phospholipid, and pantothenyl alcohol was added as an acceptor in a transfer reaction. The same reaction, extraction and purification were carried out as in Example 2. As a result, 25 mg of a transfer product was obtained. The IR spectrum of this compound is shown in Table 6 (Run No. 9).

The above procedure was repeated using the other primary alcohols indicated in Table 6. The results are shown in Table 6 (Runs Nos. 1 to 8 and 10 to 24).

TABLE 6

Infrared spectra of transfer products of 1,3-dihexadecanoyl-glycerol-2-phosphoric acid with various alcohols

| Run No. | Alcohol as an acceptor in a transfer reaction | IR $\nu_{max}$ |
|---|---|---|
| 1 | 1-Heptanol | 2920, 2850, 1735, 1465, 1380, 1220, 1175, 1060, 1010, 850, 720 |
| 2 | 1-Hexadecanol | 2920, 2850, 1735, 1465, 1380, 1230, 1170, 1090, 1050, 840, 720 |
| 3 | 1-Docosanol | 2920, 2850, 1730, 1465, 1380, 1220, 1170, 1100, 1060, 840, 720 |
| 4 | Geraniol | 2920, 2850, 1735, 1665, 1465, 1380, 1220, 1100, 1070, 1000, 840, 720 |
| 5 | Phytol | 2920, 2850, 1735, 1665, 1465, 1380, 1220, 1095, 1070, 1005, 850, 720 |
| 6 | 1,6-hexanediol | 3400, 2920, 2850, 1735, 1465, 1380, 1220, 1180, 1090, 1010, 720 |
| 7 | 1,12-Dodecanediol | 3380, 2920, 2850, 1740, 1465, 1380, 1220, 1175, 1090, 1010, 860, 720 |
| 8 | 2-n-Butyl-2-ethyl-1,3-propanediol | 3380, 2920, 2850, 1735, 1465, 1380, 1220, 1180, 1100, 1070, 990, 840, 760, 720 |

TABLE 6-continued

Infrared spectra of transfer products of 1,3-dihexadecanoyl-glycerol-2-phosphoric acid with various alcohols

| Run No. | Alcohol as an acceptor in a transfer reaction | IR $\nu_{max}$ |
|---|---|---|
| 9 | Pantothenyl alcohol | 3360, 2920, 2850, 1735, 1640, 1540, 1465, 1380, 1220, 1180, 1060, 1010, 760, 720 |
| 10 | Diethylene glycol monobutyl ether | 2920, 2850, 1735, 1465, 1380, 1230, 1150, 1100, 1060, 1010, 860, 760, 720 |
| 11 | Monolaurin | 3400, 2920, 2850, 1735, 1465, 1380, 1230, 1180, 1110, 1060, 1010, 860, 720 |
| 12 | Benzyl alcohol | 3380, 2920, 2850, 1735, 1495, 1465, 1410, 1380, 1230, 1170, 1090, 1060, 860, 730, 695 |
| 13 | p-Chlorobenzyl alcohol | 3320, 2920, 2850, 1735, 1495, 1465, 1410, 1380, 1230, 1175, 1090, 1055, 870, 805, 720, 660 |
| 14 | β-Hydroxyethylaniline | 3380, 2920, 2850, 1735, 1605, 1500, 1465, 1380, 1230, 1175, 1065, 990, 840, 750, 720, 695 |
| 15 | 2-Hydroxyethylsalicylic acid | 3300, 2920, 2850, 1735, 1680, 1615, 1590, 1495, 1465, 1380, 1300, 1230, 1210, 1160, 1055, 900, 860, 755, 720, 695 |
| 16 | 1,4-Dihydroxy-methylcyclohexane | 3360, 2920, 2850, 1735, 1465, 1380, 1220, 1170, 1100, 1050, 860, 720 |
| 17 | 2-Naphthaleneethanol | 2920, 2850, 1735, 1465, 1380, 1230, 1150, 1100, 1055, 1010, 850, 820, 740 |
| 18 | Cortisone | 3380, 2920, 2850, 1735, 1700, 1665, 1465, 1380, 1220, 1170, 1095, 1045, 1000, 860, 740 |
| 19 | 0,0-bis(2-hydroxyethyl) tetrabromobisphenol | 3400, 2920, 2850, 1735, 1595, 1535, 1465, 1380, 1235, 1180, 1050, 985, 870, 740 |
| 20 | 2-(3-Indole)ethanol | 3400, 2920, 2850, 1730, 1675, 1600, 1585, 1465, 1380, 1245, 1110, 1070, 860, 740, 700 |
| 21 | Pyridoxine | 3350, 2920, 2850, 1730, 1540, 1465, 1380, 1220, 1195, 1170, 1070, 860, 715 |
| 22 | 5-Hydroxymethylcytosine | 2920, 2850, 1735, 1670, 1545, 1465, 1380, 1220, 1170, 1065, 860, 720 |
| 23 | Thiamine | 3350, 3200, 2920, 2850, 1735, 1660, 1600, 1560, 1465, 1450, 1380, 1230, 1170, 1100, 1065, 990, 910, 820, 750, 720 |
| 24 | Adenosine | 3380, 3200, 2920, 2850, 1735, 1465, 1410, 1380, 1220, 1170, 1070, 810, 720 |

EXAMPLE 6

(Run Nos. 1 to 5)

Each of L-alpha-phosphatidyl ethanolamine, beta,-gamma-dimyristoyl (I), L-alpha-phosphatidyl N-methyl ethanolamine, beta,gamma-dimyristoyl (II), L-alpha-phosphatidyl-DL-glycerol beta, gamma-dimyristoyl (III) (the above three compounds are products of Calbiochem-Behring Co.), L-alpha-phosphatidyl serine (IV) (a product of Sigma Co.), and L-alpha-phosphatidyl ethanol, beta,gamma-dimyristoyl (V) prepared by the method of S. F. Yang, et al. (J. Biol Chem., 242, 477, 1967) was emulsified by the same method as in Example 2. Emulsions (1.5 ml) containing 50 mg of the individual phospholipids were put into separate test tubes with a ground stopper. One milliliter of a 10% diethyl ether solution of geraniol, 1 ml of 0.4M acetate buffer, 1 ml of distilled water and 0.5 ml of a 0.01M aqueous solution of calcium chloride were added, and the mixture was subjected to an ultrasonication treatment for 1 minute at 600 W and 20 KHz. One milliliter of aqueous solution of phospholipase DM (8 u/ml) was added to each of the reaction solutions, and the mixture was left to stand at 37° C. for 6 hours. The extraction and purification of the phospholipids were carried out in the same way as in Example 2 to give a geraniol ester of phosphatidic acid as a common transfer product. The amount of the product yielded was 12 mg for I, 20 mg for II, 10 ml for III, 24 mg for IV and 22 mg for V.

The IR spectrum of the product is shown in Table 7.

TABLE 7

| Run No. | Phospholipid | IR $\nu_{max}$ |
|---|---|---|
| 1 | I | 2920, 2850, 1740, 1665, 1460, 1380, 1215, 1090, 1075, 1000, 830, 720 |
| 2 | II | 2920, 2850, 1740, 1665, 1460, 1380, 1215, 1090, 1075, 1000, 830, 720 |
| 3 | III | 2920, 2850, 1740, 1665, 1460, 1380, 1215, 1090, 1075, 1000, 830, 720 |
| 4 | IV | 2920, 2850, 1740, 1665, 1460, 1380, 1215, 1090, 1075, 1000, 830, 720 |
| 5 | V | 2920, 2850, 1740, 1665, 1460, 1380, 1215, 1090, 1075, 1000, 830, 720 |

EXAMPLE 7

(Runs Nos. 1 to 21)

Each of the phospholipids I to IV within the formula (II) described in Example 1 was reacted with each of the secondary alcohols indicated in Table 8 below in the presence of the phospholipase DM in accordance with the method of confirming the formation of a transfer product (phospholipid-secondary alcohol derivative) by TLC described in Example 1 to confirm the formation of a transfer product. The Rf values of the tranfer products in these runs are shown in Table 8 below.

COMPARATIVE EXAMPLE 2

Example 7 was repeated except that known phospholipase D (P-L Biochemicals, Inc.) derived from cabbage was used instead of the phospholipase DM. With all of the secondary alcohols shown in Table 8, transfer products were not formed.

TABLE 8

| | | Rf value of the transfer product | | | |
|---|---|---|---|---|---|
| Run No. | Secondary alcohol added | Substrate I | Substrate II | Substrate III | Substrate IV |
| 1 | iso-Propanol | 0.65 | 0.57 | 0.48 | 0.65 |
| 2 | 2-Butanol | 0.66 | 0.57 | 0.50 | 0.65 |
| 3 | 2-Pentanol | 0.68 | 0.60 | 0.50 | 0.67 |
| 4 | 2-Hexanol | 0.67 | 0.62 | 0.50 | 0.67 |
| 5 | 2-heptanol | 0.70 | 0.62 | 0.51 | 0.66 |
| 6 | 2-Octanol | 0.70 | 0.60 | 0.52 | 0.67 |
| 7 | 2-Decanol | 0.70 | 0.62 | 0.52 | 0.68 |
| 8 | 2,3-Butanediol | 0.54 | 0.46 | 0.40 | 0.53 |
| 9 | 2-Butyl-2,4-pentanediol | 0.62 | 0.57 | 0.48 | 0.62 |
| 10 | 1-Chloro-2-propanol | 0.65 | 0.59 | 0.50 | 0.67 |
| 11 | 1-Amino-2-propanol | 0.51 | 0.42 | 0.37 | 0.50 |
| 12 | Diisopropanolamine | 0.50 | 0.46 | 0.35 | 0.47 |
| 13 | 3-Hydroxy-2-butanone | 0.55 | 0.46 | 0.40 | 0.53 |
| 14 | Ethyl lactate | 0.56 | 0.46 | 0.38 | 0.56 |
| 15 | Dipropylene glycol | 0.50 | 0.38 | 0.37 | 0.51 |
| 16 | 1-Phenylethanol | 0.66 | 0.59 | 0.48 | 0.67 |
| 17 | 1-Phenyl-2-propanol | 0.68 | 0.60 | 0.51 | 0.67 |
| 18 | α-(1-Aminoethyl)-p-hydroxybenzyl alcohol | 0.42 | 0.38 | 0.36 | 0.42 |

TABLE 8-continued

| Run No. | Secondary alcohol added | Rf value of the transfer product | | | |
|---|---|---|---|---|---|
| | | Substrate I | Substrate II | Substrate III | Substrate IV |
| 19 | Cyclohexanol | 0.68 | 0.58 | 0.52 | 0.66 |
| 20 | 1,4-Dihydroxy-cyclohexane | 0.62 | 0.55 | 0.50 | 0.62 |
| 21 | Diphenylmethanol | 0.67 | 0.62 | 0.52 | 0.66 |
| | Not added | | | | |
| | Phosphatidic acid | 0.59 | 0.49 | 0.44 | 0.58 |
| | Substrate | 0.27 | 0.25 | 0.20 | 0.30 |

EXAMPLE 8

(Runs Nos. 1 to 7)

Four hundred milligrams of L-alpha-lecithin, beta,-gamma-dimyristoyl (a product of Sigma Chemical Company; purity 98%), 1 ml of diethyl ether and 10 ml of distilled water were put in an ultrasonication cell, and with ice cooling, subjected to an ultrasonication treatment for 5 minutes at 600 W and 20 KHz to obtain a milk-white emulsion.

Two milliliters of the lecithin emulsion (80 mg of lecithin), 2 ml of 0.4M acetic acid buffer (pH 5.7), 1 ml of a 0.1M aqueous solution of calcium chloride and 2 ml of a 10% aqueous solution of 1-amino-2-propanol hydrochloride were put in a test tube having a ground stopper, and 2 ml of an aqueous solution of phospholipase DM (5 u/ml) was added and well mixed. The mixture was left to stand at 37° C. for 4 hours. To the reaction mixture was added 0.5 ml of 0.5N hydrochloric acid to stop the reaction. Then, 15 ml of a mixture of chloroform and methanol (2:1) was added and vigorously mixed to extract phospholipids. The mixture was centrifuged for 10 minutes at 2000 x g, and the lower chloroform layer was separated. Chloroform (10 ml) was further added to the upper aqueous layer, and the same extraction operation as above was carried out. The chloroform layers were combined, and washed with 10 ml of 0.02N hydrochloric acid. The chloroform layer was separated from the mixture again by centrifugation, dried under reduced pressure, and dissolved in 1 ml of a mixture of n-hexane, 2-propanol and water (60:80:7).

Twenty microliters of the solution (sample) was spotted on a thin layer of silica gel (Funagel, a product of Funakoshi Yakuhin K. K.), and the silica gel layer was developed with a solvent system composed of diisobutyl ketone, acetic acid and water (40:25:5). Three phospholipids were detected. A spot having the largest Rf value agreed in Rf value with phosphatidic acid. On the other hand, a spot having the smallest Rf value agreed in Rf value with lecithin. The intermediate spot alone developed a color upon reaction with the ninhydrin reagent.

The sample was purified by high-performance liquid chromatography. The column used was a Radial-Pak cartridge silica, 8 mm×10 cm, (made by Waters Co.), and the eluent used was a mixture of n-hexane, 2-propanol and water (60:80:7). The flow rate was 2 ml/min. For the detection of peaks, a 441-type ultraviolet detector (Waters Co.) for determining an absorption at 214 nm, and an R401-type differential refractometer (made by Waters Co.) were used. The sample was added four times in an amount of 0.25 ml each time.

This operation could effect fractionation of two phospholipids, i.e. phosphatidic acid and a 1-amino-2-propanol ester of phosphatidic acid. The undecomposed lecithin adsorbed on the column was eluted by using a mixture of n-hexane, 2-propanol and water (60:80:14) as an eluent. The three phospholipids were each found to be a single entity by TLC and high-performance liquid chromatography. The proportions of the three lipids were as follows:

Phosphatidic acid: about 30 mole %
Transfer product: about 30 mole %
Lecithin: about 40 mole %

About 20 mg of a 1-amino-2-propanol ester of phosphatidic acid was obtained. The IR spectrum of this compound was measured by a liquid film method using an infrared spectrophotometer (Model A202 made by Nippon Bunko K. K.). The results are shown in Table 9 (Run No. 4).

The above procedure was repeated using the other secondary alcohols shown in Table 9. The results are shown in Table 9 (Runs Nos. 1 to 3 and 5 to 7). The secondary alcohols were added as a solution in water, diethyl ether or acetone selected as required depending upon the solubilites of the alcohols.

TABLE 9

Infrared spectra of transfer products of 1,2-ditetradecanoyl-sn-glycerol-3-phosphoric acid with various alcohols

| Run No. | Alcohol as an acceptor in a transfer reaction | IR $\nu_{max}$ |
|---|---|---|
| 1 | 2-Butanol | 2920, 2850, 1735, 1465, 1380, 1235, 1170, 1100, 1070, 830, 720 |
| 2 | 2-Decanol | 2920, 2850, 1735, 1465, 1380, 1230, 1170, 1105, 1075, 830, 720 |
| 3 | 2,3-Butanediol | 3400, 2920, 2850, 1735, 1465, 1380, 1230, 1170, 1105, 1065, 850, 720 |
| 4 | 1-Amino-2-propanol | 3400, 2920, 2850, 1740, 1630, 1545, 1470, 1380, 1230, 1770, 1095, 1070, 970, 880, 825, 750, 720 |
| 5 | Ethyl lactate | 3420, 2920, 2850, 1735, 1465, 1380, 1265, 1230, 1130, 1070, 1015, 930, 860, 720 |
| 6 | 1-Phenyl-2-propanol | 2920, 2860, 1740, 1500, 1460, 1380, 1240, 1170, 1105, 1060, 995, 830, 740, 700 |
| 7 | Cyclohexanol | 2930, 2860, 1740, 1465, 1380, 1235, 1165, 1105, 1050, 1015, 890, 720 |

EXAMPLE 9

(Runs Nos. 1 to 7)

A mixture of 400 mg of L-alpha-lecithin, beta,gamma-dihexadecyl (a product of Calbiochem-Behring), 1 ml of diethyl ether and 10 ml of distilled water was emulsified by the same method as in Example 8. Using 2 ml of the emulsion, the same reaction as in Example 8 was carried out except that a 10% diethyl ether solution of cyclohexanol was used as a secondary alcohol. The reaction mixture was worked up in the same way as in Example 8 to give 18 mg of a transfer product. The IR spectrum of this compound is shown in Table 10 (Run No. 7).

The above procedure was repeated using the other secondary alcohols shown in Table 10. The results are shown in Table 10 (Runs Nos. 1 to 6).

TABLE 10

IR spectra of transfer products of 1,2-diheadecyl-sn-glycerol-3-phosphoric acid with various alcohol

| Run No. | Alcohol as an acceptor in a transfer reaction | IR $\nu_{max}$ |
|---|---|---|
| 1 | 2-Butanol | 2920, 2850, 1465, 1380, 1230, 1110, 1040, 860, 720 |
| 2 | 2-Decanol | 2920, 2850, 1465, 1380, 1235, 1105, 1035, 880, 720 |
| 3 | 2,3-Butanediol | 3400, 2920, 2850, 1465, 1380, 1235, 1100, 1040, 875, 755, 720 |
| 4 | 1-Amino-2-propanol | 3400, 2920, 2850, 1635, 1545, 1465, 1380, 1230, 1105, 1045, 970, 880, 750, 720 |
| 5 | Ethyl lactate | 3420, 2920, 2850, 1735, 1465, 1380, 1260, 1230, 1120, 1045, 930, 860, 720 |
| 6 | 1-Phenyl-2-propanol | 3400, 2920, 2850, 1495, 1460, 1380, 1230, 1115, 1000, 880, 830, 740, 700 |
| 7 | Cyclohexanol | 2930, 2860, 1470, 1380, 1230, 1120, 1020, 890, 760, 720 |

EXAMPLE 10

(Runs Nos. 1 to 7)

Four hundred milligrams of L-alpha-lecithin, beta,-gamma-hexadecylidine (a product of Calbiochem-Behring Co.) was emulsified by the same method as in Example 8 to form an emulsion. The emulsion in an amount corresponding to 80 mg of the phospholipid was used, and 1-phenyl-2propanol was added as an acceptor of a transfer reaction. The same reaction, extraction and purification as in Example 8 were carried out to give 22 mg of a tranfer product. The IR spectrum of this product is shown in Table 11 (Run No. 6).

The above procedure was repeated using the other secondary alcohols shown in Table 11 (Runs Nos. 1 to 5 and 7).

TABLE 11

IR spectra of transfer products of 1,2-cyclohecadecylidene-sn-glycerol-3-phosphoric acid with various alcohols

| Run No. | alcohol as an acceptor in a transfer reaction | IR $\nu_{max}$ |
|---|---|---|
| 1 | 2-Butanol | 2920, 2850, 1465, 1380, 1220, 1120, 1010, 880, 720 |
| 2 | 2-Decanol | 2920, 2850, 1465, 1380, 1220, 1125, 1030, 880, 720 |
| 3 | 2,3-Butanediol | 3400, 2920, 2850, 1465, 1380, 1225, 1110, 1080, 1010, 875, 720 |
| 4 | 1-Amino-2-propanol | 3420, 2920, 2850, 1640, 1550, 1465, 1380, 1230, 1105, 1030, 880, 750, 720 |
| 5 | Ethyl lactate | 3380, 2920, 2850, 1735, 1465, 1380, 1265, 1225, 1130, 1040, 930, 860, 720 |
| 6 | 1-Phenyl-2-propanol | 3420, 2920, 2850, 1495, 1460, 1380, 1235, 1125, 995, 880, 740, 700 |
| 7 | Cyclohexanol | 2920, 2850, 1465, 1380, 1232, 1110, 1035, 885, 760, 720 |

EXAMPLE 11

(Runs Nos. 1 to 7)

Four hundred milligrams of beta-lecithin, alpha,gamma-dihexadecanoyl (a product of CalbiochemBehring Co.) was emulsifieid in the same way as in Example 8. The emulsion in an amount corresponding to 80 mg of the phospholipid was used, and 1-amino-2-propanol was added as an acceptor of a transfer reaction. The same reaction, extraction and purification as in Example 8 were carried out to give 10 mg of a transfer product. The IR spectrum of this product is shown in Table 12 (Run No. 4).

The above procedure was repeated using the other secondary alcohols shown in Table 12. The results are shown in Table 12 (Runs Nos. 1 to 3 and 5 to 7).

TABLE 12

IR spectra of transfer products of 1,3-dihexadecanoyl-glycerol-2-phosphoric acid with various alcohols

| Run No. | Alcohol as an acceptor in a transfer reaction | IR $\nu_{max}$ |
|---|---|---|
| 1 | 2-Butanol | 2920, 2850, 1735, 1465, 1380, 1220, 1175, 1110, 1060, 845, 720 |
| 2 | 2-Decanol | 2920, 2850, 1735, 1465, 1380, 1225, 1175, 1110, 1060, 845, 720 |
| 3 | 2,3-Butanediol | 3380, 2920, 2850, 1735, 1465, 1380, 1230, 1175, 1105, 1055, 850, 720 |
| 4 | 1-Amino-2-propanol | 3420, 2920, 2850, 1735, 1640, 1545, 1465, 1380, 1220, 1180, 1060, 1000, 845, 720 |
| 5 | Ethyl lactate | 3380, 2920, 2850, 1735, 1465, 1380, 1265, 1225, 1175, 1130, 1060, 930, 855, 720 |
| 6 | 1-Phenyl-2-propanol | 3380, 2920, 2850, 1735, 1495, 1465, 1380, 1230, 1175, 1110, 1065, 990, 840, 750, 700 |
| 7 | Cyclohexanol | 2920, 2850, 1735, 1465, 1380, 1230, 1170, 1105, 1060, 1010, 880, 720 |

EXAMPLE 12

(Runs Nos. 1 to 5)

Each of the phospholipids (I) to (V) shown in Example 6 was emulsified in the same way as in Example 8. Emulsions (1.5 ml each) containing 50 mg of the individual phospholipids were put in separate test tubes equipped with a ground stopper. One milliliter of a 10% diethyl ether solution of 1-phenyl-2-propanol as an alcohol, 1 ml of 0.4M acetate buffer, 1 ml of distilled water, and 0.5 ml of a 0.01M aqueous solution of calcium chloride were added, and the reaction mixture was subjected to an ultrasonication treatment for 1 minute at 600 W and 20 KHz. One milliliter of an aqueous solution of phospholipase DM (8 u/ml) was added to each of the reaction mixtures, and the mixture was left to stand at 37° C. for 6 hours. The resulting phospholipids were extracted and purified in the same way as in Example 8, and 1-phenyl-2-propanol phosphatidate, a common transfer product, was obtained in an amount of 6 mg for (I), 8 mg for (II), 7 mg for (III), 8 mg for (IV), and 10 mg for (V). The IR spectrum of the product is shown in Table 13.

TABLE 13

| Run No. | Phospholipid | IR $\nu_{max}$ |
|---|---|---|
| 1 | I | 2920, 2850, 1740, 1500, 1460, 1380, 1240, 1170, 1105, 1060, 990, 830, 740, 770. |
| 2 | II | 2920, 2850, 1740, 1500, 1460, 1380, 1240, 170, 1105, 1060, 990, 830, 740, 770. |
| 3 | III | 2920, 2850, 1740, 1500, 1460, 1380, 1240, 1170, 1105, 1060, 990, 830, 740, 770. |

TABLE 13-continued

| Run No. | Phospholipid | IR $\nu_{max}$ |
|---|---|---|
| 4 | IV | 2920, 2850, 1740, 1500, 1460, 1380, 1240, 1170, 1105, 1060, 990, 830, 740, 770. |
| 5 | V | 2920, 2850, 2740, 1500, 1460, 1380, 1240, 1170, 1105, 1060, 990, 830, 740, 770. |

What we claim is:

1. A process for producing a primary or secondary alcohol derivative of a phospholipid represented by the following formula (I)

$$A-O-\underset{\underset{OH}{|}}{\overset{\overset{O}{\|}}{P}}-O-R \qquad (I)$$

wherein A and R are as defined below, which comprises reacting a phospholipid represented by the following formula (II)

$$A-O-\underset{\underset{OH}{|}}{\overset{\overset{O}{\|}}{P}}-O-B \qquad (II)$$

wherein A is a moiety represented by the following formula (i)

$$\begin{array}{l} CH_2-R_1 \\ | \\ CH-R_2 \\ | \\ CH_2- \end{array} \qquad (i)$$

or the following formula (ii)

$$\begin{array}{l} CH_2-R_1 \\ | \\ CH- \\ | \\ CH_2-R_2 \end{array} \qquad (ii)$$

in which $R_1$ and $R_2$ both represent $-O-COR_{11}$ or $-O-R_{12}$, or $R_1$ and $R_2$ in formula (i) together represent

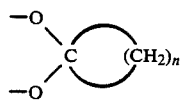

in which n represents a number of from 11 to 19, and $R_{11}$ and $R_{12}$ are identical or different and each represents a saturated or unsaturated saturated aliphatic hydrocarbon group having 7 to 21 carbon atoms, and B represents the group $-(CH_2)_2N^+(CH_3)_3$, $-(CH_2)_2NH_2$, $-CH_2CH(NH_2)COOH$, $-CH_2CH_2NH(CH_3)$, $-CH_2CH_2N(CH_3)_2$, $-CH_2CHOHCH_2OH$ or $-(CH_2)_mH$ in which m represents a number of from 1 to 5, with a primary or secondary alcohol selected from the group consisting of (1) primary alcohols containing a residue R of a saturated or unsaturated aliphatic or aromatic hydrocarbon having 6 to 26 carbon atoms said hydrocarbon residue residue being unsubstituted or substituted by a substituent selected from the group consisting of halogen, amino, acetyl, carboxyl and hydroxyl, provided that when the residue R is a residue of a saturated aliphatic hydrocarbon having 6 carbon atoms, the residue is substituted by a said substituent, or a residue R of said aliphatic or aromatic hydrocarbon having in the molecule a linkage selected from ether, ester and amide linkages, (2) primary alcohols having a residue R of a pregnane-type steroidal compound, (3) primary alcohols having a residue R of a heterocyclic compound selected from the group consisting of a galactono-gamma-lactone, N-(2-hydroxyethyl)-phthalimide, 2-(3-indole)ethanol, 2-(2-hydroxyethyl)pyridine, pyridoxine, N-(2-hydroxyethyl)morpholine, 5-hydroxymethylcytosine, cytidine, uridine, arabinocytidine, thiamine, 2-(2-hydroxyethyl)piperazine, adenosine, guanosine and cyclocytidine, and (4) secondary alcohols having a $C_3-C_{10}$ linear or branched alkyl group R which may be substituted by a substituent selected from the group consisting of halogen, amino, acetyl, hydroxyl, mono- or dialkylamino of not more than 3 carbon atoms and phenyl, or a $C_4-C_8$ alicyclic hydrocarbon group R which may be substituted by said substituent, in the presence of phospholipase DM, said phospholipase DM having the ability to catalyze the formation of a phospholipid-primary alcohol derivative from lecithin and geraniol and the formation of a phospholipid-secondary alcohol derivative from lecithin and 2-butanol, and recovering the reaction product formed.

2. The process of claim 1 wherein the phospholipid represented by formula (II) is at least one member selected from the group consisting of lecithin, cephalin, phosphatidyl serine, phosphatidyl N-methylethanolamine, phosphatidyl glycerol, phosphatidyl N,N-dimethylethanolamine and alkyl esters of phosphatidic acid.

3. The process of claim 1 wherein the primary or secondary alcohol is a member selected from the group consisting of (1) 1-heptanol, 1-octanol, 2-ethyl-1-hexanol, 1-nonanol, 1-decanol, 1-undecanol, 1-dodecanol, 1-tetradecanol, 1-hexadecanol, 1-octadecanol, 1-docosanol, 1-eicosanol, 1-hexacosanol, geraniol, citronellol, farnesol, phytol, 1,6-hexanediol, 1,2,6-hexanetriol, sorbitol, mannitol, 2-n-butyl-2-ethyl-1,3-propanediol, 2-ethyl-1,3-hexanediol, 1,1,1-tris(-hydroxymethyl)propane, 3,3-bis(hydroxymethyl)-heptane, 1,10-decanediol, 1,12-dodecanediol, trimethylol propanol, dipentaerythritol, 6-amino-1-hexanol, triethanolamine, N-butyl-diethanolamine, serine ethyl ester, dihydroxyethylglycine, sphingosine, N-methyl pentanolamine, N-methyl hexanolamine, N-ethyl butanolamine, N-ethyl pentanolamine, N-ethyl hexanolamine, N-propyl propanolamine, N-propyl butanolamine, N-propyl pentanolamine, N-propyl hexanolamine, N-butyl ethanolamine, N-butyl propanolamine, N-butyl butanolamine, N-butyl pentanolamine, N-butyl hexanolamine, N-pentyl ethanolamine, N-hexyl ethanolamine, N,N-dimethyl butanolamine, N,N-dimethyl pentanolamine, N,N-dimethyl hexanolamine, N,N-diethyl ethanolamine, N,N-diethyl propanolamine, N,N-diethyl butanolamine, N,N-diethyl pentanolamine, N,N-diethyl hexanolamine, N,N,-dipropyl ethanolamine, N,N-dipropyl propanolamine, N,N-dipropyl butanolamine, N,N-dipropyl pentanolamine, N,N-dipropyl hexanolamine, N,N-dibutyl propanolamine, N,N-dibutyl butanolamine, N,N-dibutyl pentanolamine, N,N-dibutyl hexanolamine, N,N-dipentyl ethanolamine, N,N-dihexyl ethanolamine, N,N,N-trimethyl propanolamine, N,N,N-trimethyl butanolamine, N,N,N-trimethyl pentanolamine, N,N,N-trimethyl hexanolamine, N,N,N-triethyl ethanolamine, N,N,N-triethyl propanolamine, N,N,N-triethyl butanolamine, N,N,N-triethyl pentanolamine, N,N,N-triethyl hexanolamine, N,N,N-tripropyl ethanolamine, N,N,N-tripropyl propanol amine, N,N,N-tripropyl butanolamine, N,N,N-tripropyl pentanolamine, N,N,N-tripropyl hexanolamine, N,N,N-tributyl ethanolamine, N,N,N-tributyl propanolamine, N,N,N-tributyl butanolamine, N,N,N-tributyl pentanolamine, N,N,N-tributyl hexanolamine, N,N,N-tripentyl ethanolamine, N,N,N-trihexyl ethanolamine, N,N-dibutyl ethanolamine, N-(3-aminopropyl)diethanolamine, 16-hydroxyhexadecanoic acid, gluconic acid, monolaurin, monoolein, 1,2-dilaurin, 1,2-distearin, 2-hydroxyethyl methacrylate, ethylene glycol monolaurate, diethylene glycol monolaurate, ethylene glycol monostearate, diethylene glycol monostearate, ethylene glycol monooleate, diethylene glycol monooleate, ethylene glycol monoplamitate, diethylene glycol monoplamitate, pantothenyl alcohol, pantetheine, tri-L-serine, L-seryl-L-leucine, L-seryl-L-methionine, L-seryl-L-arginine, L-seryl-L-lysine, L-seryl-L-glutamine, N-capriloyl ethanolamine, N-caproyl ethanolamine, N-lauroyl ethanolamine, N-myristoyl ethanolamine, N-palmitoyl ethanolamine, N-stearoyl ethanolamine, N-oleoyl ethanolamine, N-palmitoleoyl ethanolamine, L-linoloyl ethanolamine, N-linolenoyl ethanolamine, N-arachidonoyl ethanolamine, N-eicosanoyl ethanolamine, N-docosanoyl ethanolamine, L-seryl-L-histidine, and L-seryl-L-tryptophan, triethylene glycol, diethylene glycol monobutyl ether, ethylene glycol monolauryl ether, diethylene glycol monolauryl ether, ethylene glycol monocetyl ether, diethylene glycol monocetyl ether, ethylene glycol monostearyl ether, diethylene glycol monostearyl ether, ethylene glycol monooleyl ether, diethylene glycol mono oleyl ether, ethylene glycol monobutyl ether, ethylene glycol mono(2-diethylaminoethyl) ether, ethylene glycol monohexyl ether, ethylene glycol monotolyl ether, diethylene glycol monoethyl ether, diethylene glycol monohexyl ether, tetraethylene glycol, pentaethylene glycol, hexaethylene glycol, octaethylene glycol, decaethylene glycol, dodecaethylene glycol, benzyl alcohol, beta-phenethyl alcohol, 3-phenyl-1-propanol, cinnamyl alcohol, L-seryl-L-tyrosine, L-seryl-L-phenylalanine, L-serine benzyl ester, L-serine beta-naphthylamide, N-dinitrophenyl-L-serine, N-(1-dimethylaminonaphthalene-5-sulfonyl)-L-serine, ethyelne glycol monobenzyl ether, ethylene glycol monooctylphenol ether, diethylene glycol monooctylphenol ether, ethylene glycol mononylphenol ether, diethylene glycol mononylphenol ether, p-chlorobenzyl alcohol, p-aminophenethyl alcohol, N-ethyl- N-(2-hydroxyethyl)-m-toluidine, beta-hydroxyethylaniline, N-(2-cyanoethyl)-N-(2-hydroxyethyl)aniline, N-phenyldiethanolamine, anisic alcohol, 1,4-di(2-hydroxyethoxy)benzene, ethylene glycol monophenyl ether, mephenesin, 2-hydroxyethyl salicyclic acid, ethylene glycol monochlorophenyl ether, 6-chlorohexanol, 0,0-bis(2-hydroxyethyl)tetrabromobisphenol, 2-naphthalene ethanol, retinol, and 1,4-dihydroxymethyl-cyclohexane;

(2) aldosterone, corticosterone, cortisone, dehydrocorticosterone, deoxycorticosterone, hydrocortisone, prednisolone, prednisone, tetrahydrocortisol, tetrahydrocortisone and triamcinolone;

(3) galactone-gamma-lactone, N-(2-hydroxyethyl)phthalimide, 2-(3-indole)ethanol, 2-(2-hydroxyethyl)-pyridine, pyridoxine, pyridoxal, pyridoxamine, N-(2-hydroxyethyl)morpholine, 5-hydroxymethylcytosine, cytidine, uridine, arabinocytidine, adenosine, guanosine, cyclocytidine, adenine deoxyriboside, cytosine deoxyriboside, guanine deoxyriboside, 5-hydroxymethyluracil, thyminedeoxyriboside, uracil deoxyriboside, inosine, orotidine, 2-(2-hydroxyethyl)piperazine, thiamine and toxopyrimidine; and (4) 2-propanol, 2-butanol, 2-pentanol, 3-pentanol, 4-methyl-2-pentanol, 2-hexanol, 3-hexanol, 1-hexen-3-ol, 2-heptanol, 3-heptanol, 2-octanol, 2-nonanol, 3-nonanol, 2-decanol, 3-decanol, 2,3-butanediol, 2-methyl-2,4-pentanediol, 1-chloro-2-propanol, 1-bromo-2-butanol, 1-amino-2-propanol, diisopropanolamine, 1-amino-2-butanol, 3-hydroxy-2-butanone, ethyl lactate, betahydroxybutyric acid, dipropylene glycol, 1-phenylethanol, 1-phenyl-2-propanol, p-chlorophenylmethyl carbinol, alpha-(1-aminoethyl)-p-hydroxybenzyl alcohol, diphenyl methanol, cyclobutanol, cyclopentanol, cyclohexanol, cyclooctanol, 2-chlorocyclohexanol, and 1,4-dihydroxycyclohexane.

4. The process of claim 1 wherein the reaction is carried out by contacting the phospholipid with the primary or secondary alcohol in the presence of the phospholipase DM at a temperature of about 0° C. to about 90° C.

5. The process of claim 1 wherein the phospholipase DM is immolibized phospholipase DM.

* * * * *